(12) United States Patent
Kubo et al.

(10) Patent No.: US 6,821,987 B2
(45) Date of Patent: Nov. 23, 2004

(54) QUINOLINE DERIVATIVES AND QUINAZOLINE DERIVATIVES HAVING AZOLYL GROUP

(75) Inventors: Kazuo Kubo, Takasaki (JP); Teruyuki Sakai, Takasaki (JP); Rika Nagao, Takasaki (JP); Yasunari Fujiwara, Saitama (JP); Toshiyuki Isoe, Takasaki (JP); Kazumasa Hasegawa, Takasaki (JP)

(73) Assignee: Kirin Beer Kabushiki Kaisha, Tokyo-to (JP)

( * ) Notice: Subject to any disclaimer, the term of this patent is extended or adjusted under 35 U.S.C. 154(b) by 0 days.

(21) Appl. No.: 10/132,473

(22) Filed: Apr. 26, 2002

(65) Prior Publication Data
US 2003/0087907 A1 May 8, 2003

(30) Foreign Application Priority Data
Apr. 27, 2001 (JP) ........................................ 2001-132775

(51) Int. Cl.[7] ................... C07D 401/12; C07D 401/14; A61K 31/47; A61K 31/517; A61P 9/10
(52) U.S. Cl. ........................ 514/312; 546/153; 544/183; 544/284; 544/235
(58) Field of Search ........................... 546/153; 514/312

(56) References Cited

U.S. PATENT DOCUMENTS 6,143,764 A    11/2000   Kubo et al. ................. 514/312

FOREIGN PATENT DOCUMENTS

| EP | 1 153 920 A1 | 11/2001 |
|----|---|---|
| JP | 11-158149 | 6/1989 |
| JP | 2002-30083 | 1/2002 |
| JP | WO 02/032872 * | 4/2002 |
| WO | WO 97/173329 | 5/1997 |
| WO | WO 99/32106 | 7/1999 |
| WO | WO 99/32111 | 7/1999 |
| WO | WO 00/43366 | 7/2000 |
| WO | WO 01/47890 A1 | 7/2001 |
| WO | WO 02/088110 A1 | 11/2002 |

* cited by examiner

*Primary Examiner*—Mark L. Berch
*Assistant Examiner*—Kahsay Habte
(74) *Attorney, Agent, or Firm*—Oblon, Spivak, McClelland, Maier & Neustadt, P.C.

(57) ABSTRACT

An object of the present invention is to provide compounds having potent antitumor activity. The compounds according to the present invention are compounds represented by formula (I) or pharmaceutically acceptable salts or solvates thereof:

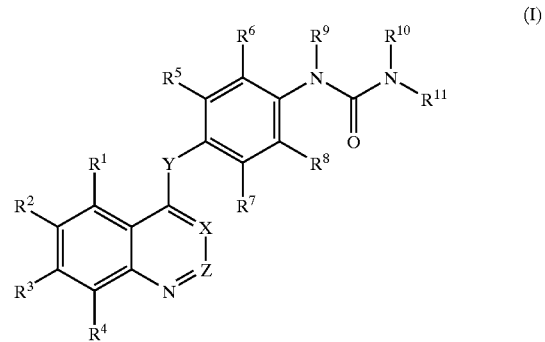

(I)

wherein X and Z represent CH or N; Y represents O or S; $R^1$, $R^2$, and $R^3$ represent H, alkoxy or the like; $R^4$ represents H; $R^5$, $R^6$, $R^7$, and $R^8$ represent H, halogen, alkoxy or the like; $R^9$ and $R^{10}$ represent H, alkyl or the like; and $R^{11}$ represents optionally substituted azolyl.

57 Claims, No Drawings

# QUINOLINE DERIVATIVES AND QUINAZOLINE DERIVATIVES HAVING AZOLYL GROUP

BACKGROUND OF THE INVENTION

1. Field of the Invention

The present invention relates to quinoline derivatives and quinazoline derivatives which have antitumor activity. More particularly, the present invention relates to quinoline derivatives and quinazoline derivatives which are therapeutically effective for diseases such as tumor, diabetic retinopathy, chronic rheumatism, psoriasis, atherosclerosis, and Kaposi's sarcoma.

2. Background Art

WO 97/17329, Japanese Patent Laid-Open No. 328782/1997, and WO 00/43366 describe quinoline derivatives and quinazoline derivatives having antitumor activity. They, however, do not disclose the compounds of the present invention.

SUMMARY OF THE INVENTION

The present inventors have found that a group of azolyl-containing quinoline derivatives and quinazoline derivatives have potent antitumor activity.

An object of the present invention is to provide compounds having potent antitumor activity.

According to the present invention, there is provided a compound represented by formula (I) or a pharmaceutically acceptable salt or solvate thereof:

wherein

X and Z each independently represent CH or N;

Y represents O or S;

$R^1$, $R^2$, and $R^3$, which may be the same or different, represent a hydrogen atom, $C_{1-6}$ alkyl, $C_{1-6}$ alkoxy, $C_{2-6}$ alkenyl, $C_{2-6}$ alkynyl, nitro, or amino and the $C_{1-6}$ alkyl, $C_{1-6}$ alkoxy, $C_{2-6}$ alkenyl, and $C_{2-6}$ alkynyl groups are optionally substituted by a halogen atom; hydroxyl; $C_{1-4}$ alkyl; $C_{1-4}$ alkoxycarbonyl; amino on which one or two hydrogen atoms are optionally substituted by $C_{1-4}$ alkyl optionally substituted by hydroxyl or $C_{1-4}$ alkoxy; group $R^{12}R^{13}N$—C(=O)—O— wherein $R^{12}$ and $R^{13}$, which may be the same or different, represent a hydrogen atom or $C_{1-4}$ alkyl optionally substituted by hydroxyl or $C_{1-4}$ alkoxy; or group $R^{14}$—(S)$_m$— wherein $R^{14}$ represents a saturated or unsaturated three- to seven-membered carbocyclic or heterocyclic group optionally substituted by $C_{1-4}$ alkyl and m is 0 or 1;

$R^4$ represents a hydrogen atom;

$R^5$, $R^6$, $R^7$, and $R^8$, which may be the same or different, represent a hydrogen atom, a halogen atom, $C_{1-4}$ alkyl, $C_{1-4}$ alkoxy, $C_{1-4}$ alkylthio, trifluoromethyl, nitro, or amino;

$R^9$ and $R^{10}$, which may be the same or different, represent a hydrogen atom, $C_{1-6}$ alkyl, or $C_{1-4}$ alkylcarbonyl and the alkyl portion of the $C_{1-6}$ alkyl or $C_{1-4}$ alkylcarbonyl group is optionally substituted by a halogen atom; $C_{1-4}$ alkoxy; amino optionally substituted by $C_{1-4}$ alkyl optionally substituted by $C_{1-4}$ alkoxy; or a saturated or unsaturated three- to seven-membered carbocyclic or heterocyclic group; and $R^{11}$ represents azolyl on which one or more hydrogen atoms are optionally substituted by a halogen atom; $C_{1-4}$ alkyl; $C_{1-4}$ alkoxy; $C_{1-4}$ alkylthio; trifluoromethyl; nitro; amino on which one or two hydrogen atoms are optionally substituted by $C_{1-4}$ alkyl group(s) which may be the same or different; $C_{1-4}$ alkoxycarbonyl $C_{1-4}$ alkyl, $C_{1-4}$ alkylcarbonyl, or $C_{3-5}$ cyclic alkyl.

The compounds according to the present invention are therapeutically effective for diseases such as tumor, diabetic retinopathy, chronic rheumatism, psoriasis, atherosclerosis, and Kaposi's sarcoma.

DETAILED DESCRIPTION OF THE INVENTION

Compound

The terms "$C_{1-6}$ alkyl" and "$C_{1-6}$ alkoxy" as used herein as a group or a part of a group respectively mean straight chain or branched chain alkyl and alkoxy having 1 to 6, preferably 1 to 4 carbon atoms.

The terms "$C_{2-6}$ alkenyl" and "$C_{2-6}$ alkynyl" as used herein as a group or a part of a group respectively mean straight chain or branched chain alkenyl and alkynyl having 2 to 6, preferably 1 to 4 carbon atoms.

Examples of $C_{1-6}$ alkyl include methyl, ethyl, n-propyl, isopropyl, n-butyl, i-butyl, s-butyl, t-butyl, n-pentyl, and n-hexyl.

Examples of $C_{1-6}$ alkoxy include methoxy, ethoxy, n-propoxy, i-propoxy, n-butoxy, i-butoxy, s-butoxy, and t-butoxy.

Examples of $C_{2-6}$ alkenyl include allyl, butenyl, pentenyl, and hexenyl.

Examples of $C_{2-6}$ alkynyl include 2-propenyl, butynyl, pentynyl, and hexynyl.

Examples of $C_{3-5}$ cyclic alkyl include cyclopropyl and cyclopentyl.

The term "halogen atom" means a fluorine, chlorine, bromine, or iodine atom.

The saturated or unsaturated three- to seven-membered carbocyclic or heterocyclic ring is preferably a five- to seven-membered, more preferably five- or six-membered, saturated or unsaturated carbocyclic or heterocyclic ring.

Examples of saturated or unsaturated three- to seven-membered carbocyclic or heterocyclic rings include phenyl, cycloheptyl, cyclohexyl, and cyclopentyl.

The saturated or unsaturated three- to seven-membered heterocyclic ring contains one or more hetero-atoms selected from oxygen, nitrogen, and sulfur atoms. The term "heteroatom" used herein means an oxygen, nitrogen, or sulfur atom. Examples of saturated or unsaturated three- to seven-membered heterocyclic groups include pyridyl, piperidino, piperazino, morpholino, imidazolyl, triazolyl, tetrazolyl, oxazolyl, thiazolyl, pyrrolidinyl, and pyrazolyl.

The term "azolyl" as used herein means a five-membered saturated or unsaturated heterocyclic group containing two or more hetro-atoms, as ring atoms, selected from the group consisting of nitrogen, sulfur, and oxygen atoms, wherein at least one of the hetero-atoms is a nitrogen atom.

$R^1$ preferably represents a hydrogen atom.

The $C_{1-6}$ alkyl, $C_{1-6}$ alkoxy, $C_{2-6}$ alkenyl, and $C_{2-6}$ alkynyl groups, which may be represented by $R^1$, $R^2$, and $R^3$, are optionally substituted by group $R^{14}$—(S)m—.

The carbocyclic or heterocyclic group, which may be represented by $R^{14}$, preferably represents a saturated or unsaturated five- or six-membered carbocyclic or heterocyclic group. The carbocyclic group more preferably represents phenyl. The heterocyclic group more preferably represents a saturated or unsaturated five-membered heterocyclic group containing one to four nitrogen atoms or a saturated or unsaturated six-membered heterocyclic group containing one or two hetero-atoms selected from nitrogen and oxygen atoms. More specifically, the hetero-atom constituting the six-membered heterocyclic group may be one nitrogen atom and one oxygen atom, or one or two nitrogen atoms.

When m is 0 (zero), —(S)m — represents a bond.

A substituted $C_{1-6}$ alkoxy group, which may be represented by $R^1$, $R^2$, and $R^3$, preferably represents group $R^{31}$—$(CH_2)p$—O— wherein $R^{31}$ represents a halogen atom; hydroxyl; $C_{1-4}$ alkoxy; $C_{1-4}$ alkoxycarbonyl; amino on which one or two hydrogen atoms each are optionally substituted by $C_{1-4}$ alkyl optionally substituted by hydroxyl or $C_{1-4}$ alkoxy; group $R^{12}R^{13}N$—C(=O)—O— wherein $R^{12}$ and $R^{13}$ are as defined in formula (I); or group $R^{14}$—(S)m— wherein $R^{14}$ is as defined in formula (I), and p is an integer of 1 to 6, preferably 1 to 4, more preferably 1 or 2.

$R^2$ and $R^3$ preferably represent $C_{1-4}$ alkoxy, more preferably methoxy.

X preferably represents N or CH, and Z preferably represents CH.

Preferably, at least one of $R^5$, $R^6$, $R^7$, and $R^8$ represents a halogen atom.

Preferably, at least one of $R^5$, $R^6$, $R^7$, and $R^8$ represents a chlorine or fluorine atom.

Preferably, at least one of $R^5$, $R^6$, $R^7$, and $R^8$ represents $C_{1-4}$ alkyl.

Preferably, at least one of $R^5$, $R^6$, $R^7$, and $R^8$ represents $C_{1-4}$ alkoxy.

Preferably, at least one of $R^5$, $R^6$, $R^7$, and $R^8$ represents $C_{1-4}$ alkylthio, trifluoromethyl, nitro, or amino.

Preferably, $R^5$ and $R^6$ represent a halogen atom, more preferably a chlorine or fluorine atom, $C_{1-4}$ alkyl, $C_{1-4}$ alkoxy, $C_{1-4}$ alkylthio, trifluoromethyl, nitro, or amino, and $R^7$ and $R^8$ represent a hydrogen atom.

$R^1$ and $R^{10}$ preferably represent a hydrogen atom.

$R^{11}$ preferably represents group (i):

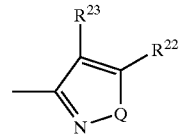

(i)

wherein Q represents O, S, or NH, and $R^{22}$ and $R^{23}$, which may be the same or different, represent a hydrogen atom; a halogen atom; $C_{1-4}$ alkyl; $C_{1-4}$ alkoxy; $C_{1-4}$ alkylthio; trifluoromethyl; nitro; amino on which one or two hydrogen atoms are optionally substituted by $C_{1-4}$ alkyl group(s) which may be the same or different; $C_{1-4}$ alkoxycarbonyl $C_{1-4}$ alkyl; $C_{1-4}$ alkylcarbonyl; or $C_{3-5}$ cyclic alkyl.

$R^{11}$ preferably represents group (ii):

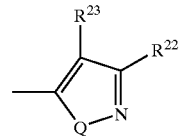

(ii)

wherein Q represents O, S, or NH, and $R^{22}$ and $R^{23}$, which may be the same or different, represent a hydrogen atom; a halogen atom; $C_{1-4}$ alkyl; $C_{1-4}$ alkoxy; $C_{1-4}$ alkylthio; trifluoromethyl; nitro; amino on which one or two hydrogen atoms are optionally substituted by $C_{1-4}$ alkyl group(s) which may be the same or different; $C_{1-4}$ alkoxycarbonyl $C_{1-4}$ alkyl; $C_{1-4}$ alkylcarbonyl; or $C_{3-5}$ cyclic alkyl.

$R^{11}$ preferably represents group (iii):

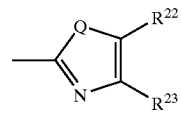

(iii)

wherein Q represents O, S, or NH, and $R^{22}$ and $R^{23}$, which may be the same or different, represent a hydrogen atom; a halogen atom; $C_{1-4}$ alkyl; $C_{1-4}$ alkoxy; $C_{1-4}$ alkylthio; trifluoromethyl; nitro; amino on which one or two hydrogen atoms are optionally substituted by $C_{1-4}$ alkyl group(s) which may be the same or different; $C_{1-4}$ alkoxycarbonyl $C_{1-4}$ alkyl; $C_{1-4}$ alkylcarbonyl; or $C_{3-5}$ cyclic alkyl.

$R^{11}$ preferably represents group (iv):

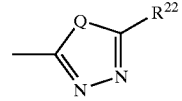

(iv)

wherein Q represents O, S, or NH, and $R^{22}$ represents a hydrogen atom; a halogen atom; $C_{1-4}$ alkyl; $C_{1-4}$ alkoxy; $C_{1-4}$ alkylthio; trifluoromethyl; nitro; amino on which one or two hydrogen atoms are optionally substituted by $C_{1-4}$ alkyl group(s) which may be the same or different; $C_{1-4}$ alkoxycarbonyl $C_{1-4}$ alkyl; $C_{1-4}$ alkylcarbonyl; or $C_{3-5}$ cyclic alkyl.

In groups (i) and (ii), $R^{23}$ preferably represents a hydrogen atom.

$R^{11}$ preferably represents optionally substituted azolyl selected from the group consisting of imidazolyl, oxazolyl, thiazolyl, pyrazolyl, isoxazolyl, isothiazolyl, 1,3,4-thiadiazolyl, 1,2,4-thiadiazolyl, 1,2,4-oxadiazolyl, and 1,3,4-oxadiazolyl.

A preferred group of compounds represented by formula (I) include compounds represented by formula (Ia):

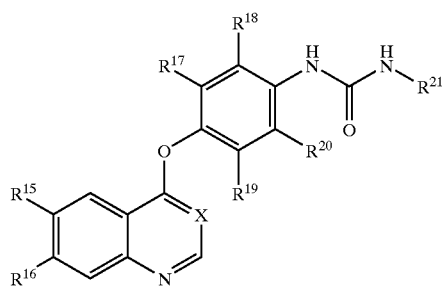

(Ia)

wherein
X represents CH or N,
$R^{15}$ and $R^{16}$, which may be the same or different, represent $C_{1-6}$ alkoxy,
$R^{17}$, $R^{18}$, $R^{19}$, and $R^{20}$, which may be the same or different, represent a hydrogen atom, a halogen atom, $C_{1-4}$ alkyl, $C_{1-4}$ alkoxy, $C_{1-4}$ alkylthio, trifluoromethyl, nitro, or amino,
$R^{21}$ represents azolyl on which one or more hydrogen atoms are optionally substituted by a halogen atom; $C_{1-4}$ alkyl; $C_{1-4}$ alkoxy; $C_{1-4}$ alkylthio; trifluoromethyl; nitro; amino on which one or two hydrogen atoms are optionally substituted by $C_{1-4}$ alkyl group(s) which may be the same or different; $C_{1-4}$ alkoxycarbonyl $C_{1-4}$ alkyl; $C_{1-4}$ alkylcarbonyl; or $C_{3-5}$ cyclic alkyl.

$R^{15}$ and $R^{16}$ preferably represent methoxy.

Preferably, at least one of $R^{17}$, $R_{18}$, $R^{19}$, and $R^{20}$ represents a halogen atom.

Preferably, at least one of $R^{17}$, $R^{18}$, $R^{19}$, and $R^{20}$ represents a chlorine or fluorine atom.

Preferably, at least one of $R^{17}$, $R^{18}$, $R^{19}$, and $R^{20}$ represents $C_{1-4}$ alkyl.

Preferably, at least one of $R^{17}$, $R^{18}$, $R^{19}$, and $R^{20}$ represents $C_{1-4}$ alkoxy.

Preferably, at least one of $R^{17}$, $R^{18}$, R19, and $R^{20}$ represents $C_{1-4}$ alkylthio, trifluoromethyl, nitro, or amino.

Preferably, $R^{17}$ and $R^{18}$ represent a halogen atom, more preferably a chlorine or fluorine atom, $C_{1-4}$alkyl, $C_{1-4}$ alkoxy, $C_{1-4}$ alkylthio, trifluoromethyl, nitro, or amino, and $R^{19}$ and $R^{20}$ represent a hydrogen atom.

$R^{21}$ preferably represents group (i), (ii), (iii), or (iv).

$R^{21}$ preferably represents optionally substituted azolyl selected from the group consisting of imidazolyl, oxazolyl, thiazolyl, pyrazolyl, isoxazolyl, isothiazolyl, 1,3,4-thiadiazolyl, 1,2,4-thiadiazolyl, 1,2,4-oxadiazolyl, and 1,3,4-oxadiazolyl.

A group of more preferred compounds represented by formula (I) include compounds represented by formula (Ib):

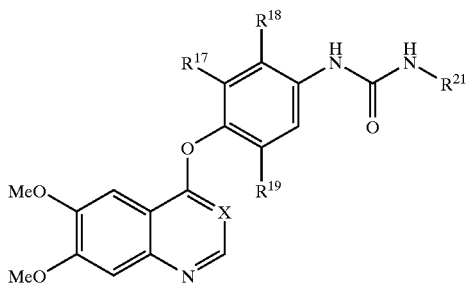

(Ib)

wherein MeO represents methoxy; X represents CH or N; $R^{17}$, $R^{18}$, and $R^{19}$, which may be the same or different, represent a hydrogen atom, a halogen atom, $C_{1-4}$ alkyl, $C_{1-4}$ alkoxy, $C_{1-4}$ alkylthio, trifluoromethyl, nitro, or amino; and $R^{21}$ represents group (i),(ii),(iii), or (iv).

In formula (Ib), preferably, $R^{21}$ represents group (i) wherein Q represents O, more preferably, both $R^{22}$ and $R^{23}$ represent a hydrogen atom, or one of $R^{22}$ and $R^{23}$ represents a hydrogen atom and the other represents $C_{1-4}$ alkyl.

In formula (Ib), preferably, $R^{21}$ represents group (iii) wherein Q represents S, more preferably, both $R^{22}$ and $R^{23}$ represent a hydrogen atom, or one of $R^{22}$ and $R^{23}$ represents a hydrogen atom and the other represents $C_{1-4}$ alkyl.

Specific examples of the compounds according to the present invention include compounds prepared in Examples 1 to 75.

More preferred compounds according to the present invention include the following compounds. Numerical values in parentheses indicate Example No.

(4) N-{2-chloro-4-[(6,7-dimethoxy-4-quinolyl)oxy]-phenyl}-N'-(5-methyl-3-isoxazolyl)urea;
(27) N-{4-[(6,7-dimethoxy-4-quinolyl)oxy]-2-fluorophenyl}-N'-(1,3-thiazol-2-yl)urea;
(28) N-{4-[(6,7-dimethoxy-4-quinolyl)oxy]-2-fluorophenyl}-N'-(4-methyl-1,3-thiazol-2-yl)urea; and
(38) N-{2-chloro-4-[(6,7-dimethoxy-4-quinazolinyl)-oxy]phenyl}-N'-(1,3-thiazol-2-yl)urea.

The compounds according to the present invention may form pharmaceutically acceptable salts thereof. Preferred examples of such salts include: alkali metal or alkaline earth metal salts such as sodium salts, potassium salts or calcium salts; hydrohalogenic acid salts such as hydrofluoride salts, hydrochloride salts, hydrobromide salts, or hydroiodide salts; inorganic acid salts such as nitric acid salts, perchloric acid salts, sulfuric acid salts, or phosphoric acid salts; lower alkylsulfonic acid salts such as methanesulfonic acid salts, trifluoromethanesulfonic acid salts, or ethanesulfonic acid salts; arylsulfonic acid salts such as benzenesulfonic acid salts or p-toluenesulfonic acid salts; organic acid salts such as fumaric acid salts, succinic acid salts, citric acid salts, tartaric acid salts, oxalic acid salts, maleic acid salts, acetic acid salts, malic acid salts, lactic acid salts, or ascorbic acid salts; and amino acid salts such as glycine salts, phenylalanine salts, glutamic acid salts, or aspartic acid salts.

Compounds of the present invention can be produced, for example, according to scheme 1 and scheme 2.

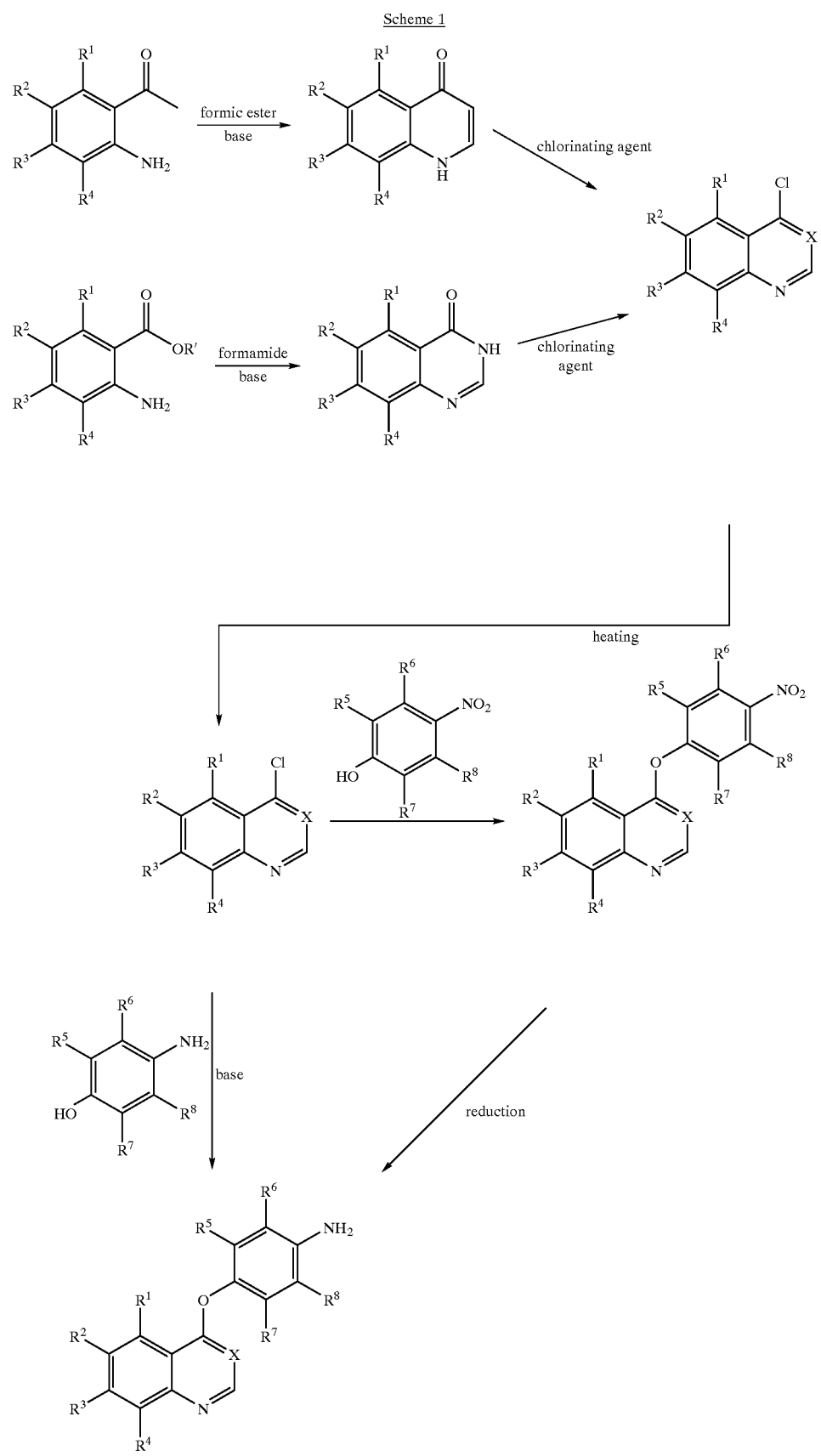

wherein R' represents $C_{1-6}$ alkyl or the like, and $R^1$, $R^2$, $R^3$, $R^4$, $R^5$, $R^6$, $R^7$, $R^8$, and X are as defined in formula (I).

Starting compounds necessary for the synthesis of the compounds according to the present invention are commercially available or may be easily produced by a conventional method. For example, a 4-chloroquinoline derivative can be synthesized by a conventional method as described, for example, in Org. Synth. Col. Vol. 3, 272 (1955), Acta Chim. Hung., 112, 241 (1983), or WO 98/47873.

Alternatively, the 4-chloroquinazoline derivative may be produced by first (1) reacting a benzoic ester with formamide to give a quinazolone derivative and then (2) heating the 4-quinazolone derivative in the presence of phosphorus oxychloride using toluene or sulfolane as a solvent. The quinazolone derivative is generally synthesized in the presence of a solvent such as a benzoic ester, sodium methoxide, formamide, N,N-dimethyl formamide, or methanol.

Next, a 4-(aminophenoxy)quinoline derivative or a corresponding quinazoline derivative can be produced by reacting nitrophenol with the 4-chloroquinoline derivative or corresponding quinazoline derivative in the presence or absence of a suitable solvent to synthesize a 4-(nitrophenoxy)quinoline derivative or a corresponding quinazoline derivative and then stirring the 4-(nitrophenoxy)quinoline derivative or corresponding quinazoline derivative in a suitable solvent, for example, N,N-dimethyl formamide, in the presence of a catalyst, for example, palladium hydroxide-carbon, palladium-carbon, under a hydrogen atmosphere. Alternatively, a 4-(aminophenoxy)quinoline derivative or a corresponding quinazoline derivative may be produced by reacting aminophenol with the 4-chloroquinoline derivative or corresponding quinazoline derivative in the presence of a base, for example, sodium hydride.

Alternatively, a 4-(aminophenoxy)quinazoline derivative may be produced by dissolving aminophenol in an aqueous sodium hydroxide solution and subjecting the solution to a two-phase reaction with a solution of the 4-chloroquinazoline derivative in an organic solvent in the presence of a phase transfer catalyst, for example, tetra-n-butylammonium bromide, or in the absence of the catalyst.

Scheme 2
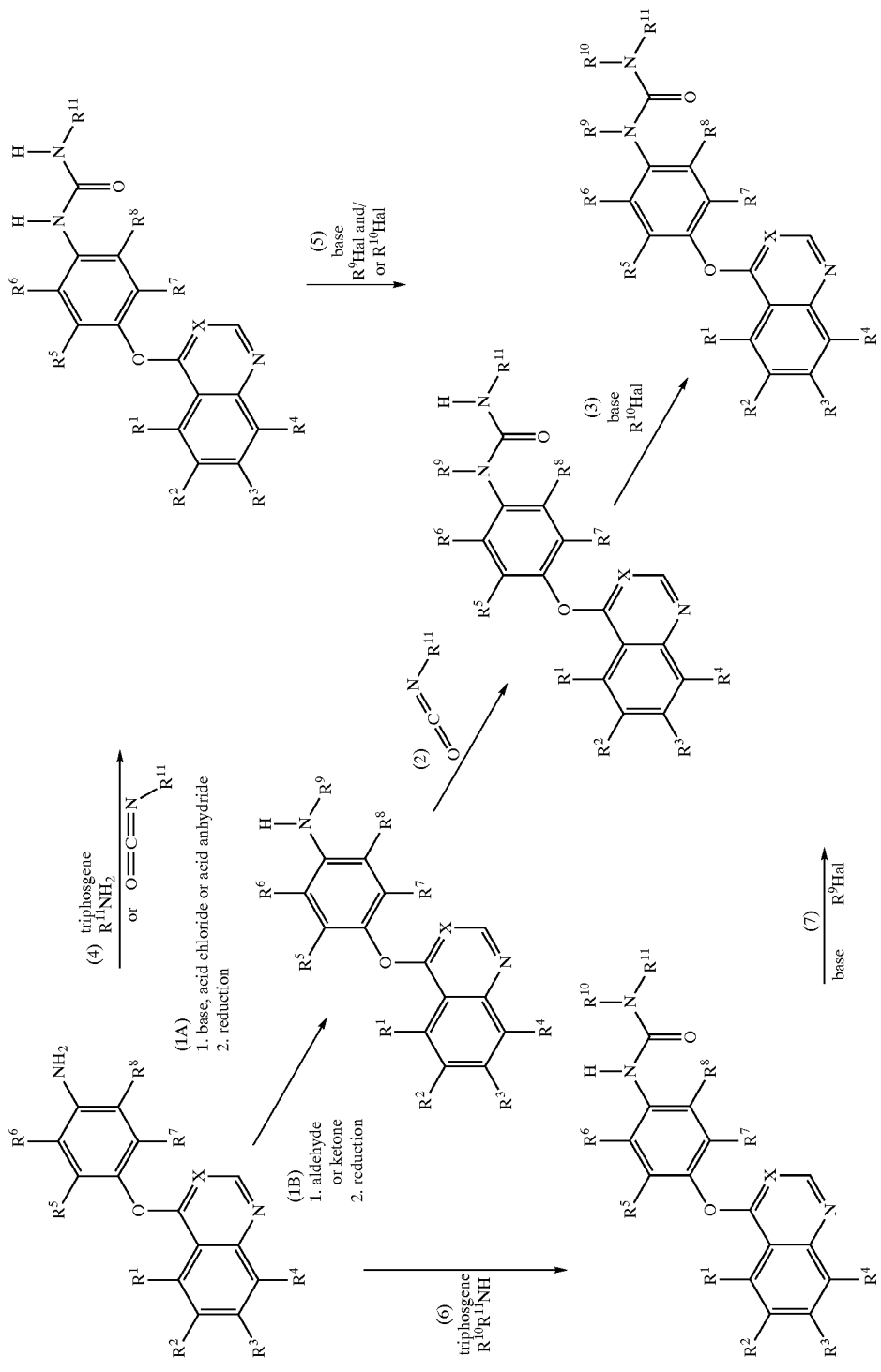

wherein Hal represents a halogen atom, and $R^1$, $R^2$, $R^3$, $R^4$, $R^5$, $R^6$, $R^7$, $R^8$, $R^9$, $R^{10}$, $R^{11}$, and X are as defined in formula (I).

A substituent can be inserted into $R^9$ by reacting the 4-(aminophenoxy)quinoline derivative or corresponding quinazoline derivative thus obtained with an acid chloride or an acid anhydride in the presence of a base and then reducing the reaction product with aluminum lithium hydride or the like (step 1A).

Alternatively, a substituent can be inserted into $R^9$ by reacting the 4-(aminophenoxy)quinoline derivative or corresponding quinazoline derivative with an aldehyde or a ketone to give an imine compound and then reacting the imine compound with sodium boron cyanohydride or the like (step 1B).

The compound represented by formula (I) can be produced by reacting the derivative having a substituent at $R^9$ with an isocyanate derivative according to a conventional method (step 2) and reacting the reaction product with a suitable alkylating agent ($R^{10}$Hal) in the presence of a base, for example, sodium hydride (step 3).

$R^9$ and $R^{10}$ may also be introduced by reacting a urea derivative, wherein $R^9$ and/or $R^{10}$ represent a hydrogen atom, with a suitable alkylating agent ($R^{10}$Hal) in the presence of a base, for example, sodium hydride, like step 3 (steps 5 and 7).

The urea derivative, wherein $R^9$ and/or $R^{10}$ represent a hydrogen atom, can be produced by reacting the 4-(aminophenoxy)quinoline derivative or corresponding quinazoline derivative prepared in scheme 1 with an isocyanate derivative according to a conventional method, or by adding triphosgene to the 4-(aminophenoxy)quinoline derivative or corresponding quinazoline derivative in the presence of a base, for example, triethylamine, and then reacting the mixture with a suitable amine derivative ($R^{11}NH_2$ or $R^{10}R^{11}NH$) (steps 4 and 6).

The compound represented by formula (I), wherein Y represents S, can be produced by reacting an aminothiophenol derivative with a 4-chloroquinoline derivative or a corresponding quinazoline derivative in a suitable solvent, for example, chlorobenzene according to scheme 1 to give a 4-(quinolylsulfanyl)aniline derivative or a 4-(quinazolinylsulfanyl)aniline derivative and then forming a urea portion according to scheme 2.

Use of Compounds/pharmaceutical Compositions

The compounds according to the present invention have inhibitory activity to tumor proliferation in vivo (Pharmacological Test Examples 2, 3, and 4).

Further, the compounds according to the present invention inhibit in vitro the autophosphorylation in a human KDR intracellular region caused by the stimulation of NIH3T3 cells, which stably develop human KDR, with VEGF (vascular endothelial growth factor) (Pharmacological Test Example 1). Binding of VEGF to KDR, a receptor for VEGF on a cell membrane, induces the activation of MAPK (mitogen-activated protein kinase) or the like through the autophosphorylation of the KDR intracellular region with tyrosine kinase (Shibuya M, Ito N, Claesson-Welsh L., in Curr. Topics Microbiol Immunol., 237, 59–83 (1999); and Abedi, H. and Zachary, I., J. Biol. Chem., 272, 15442–15451 (1997)). The activation of MAPK is known to play an important role in the growth of vascular endothelial cells in angiogenesis (Merenmies, J. et al., Cell Growth & Differ., 83-10 (1997); and Ferrara, N. and Davis-Smyth, T., Endocr. Rev., 18, 4–25 (1997)). Therefore, the compounds according to the present invention have angiogenesis inhibitory activity.

Angiogenesis at pathologic sites is known to be deeply involved in diseases, such as tumor, diabetic retinopathy, chronic rheumatism, psoriasis, atherosclerosis, and Kaposi's sarcoma, and metastasis of solid tumors (Folkman, J. Nature Med. 1: 27–31 (1995); Bicknell, R., Harris, A. L. Curr. Opin. Oncol. 8: 60–65 (1996)). Therefore, the compounds according to the present invention can be used in the treatment of these diseases.

According to the present invention, there is provided a pharmaceutical composition comprising the compound according to the present invention. The pharmaceutical composition according to the present invention may be used in the treatment of diseases, such as tumor, diabetic retinopathy, chronic rheumatism, psoriasis, atherosclerosis, and Kaposi's sarcoma, and metastasis of solid tumors.

The compounds according to the present invention can be administered to human and non-human animals orally or parenterally by administration routes, for example, intravenous administration, intramuscular administration, subcutaneous administration, rectal administration, or percutaneous administration. Therefore, the pharmaceutical composition comprising as an active ingredient the compound according to the present invention is formulated into suitable dosage forms according to the administration routes.

Specifically, oral preparations include tablets, capsules, powders, granules, and syrups, and parental preparations include injections, suppositories, tapes, and ointments.

These various preparations may be prepared by conventional methods, for example, with commonly used pharmaceutically acceptable carriers, such as excipients, disintegrants, binders, lubricants, colorants, and diluents.

Excipients include, for example, lactose, glucose, corn starch, sorbit, and crystalline cellulose; disintegrants include, for example, starch, sodium alginate, gelatin powder, calcium carbonate, calcium citrate, and dextrin; binders include, for example, dimethylcellulose, polyvinyl alcohol, polyvinyl ether, methylcellulose, ethylcellulose, gum arabic, gelatin, hydroxypropylcellulose, and polyvinyl pyrrolidone; lubricants include, for example, talc, magnesium stearate, polyethylene glycol, and hydrogenated vegetable oils.

In preparing the injections, if necessary, for example, buffers, pH adjustors, stabilizers, tonicity agents, and preservatives may be added.

The content of the compound according to the present invention in the pharmaceutical composition according to the present invention may vary depending on the dosage form. In general, however, the content is 0.5 to 50% by weight, preferably 1 to 20% by weight, based on the whole composition.

The dose may be appropriately determined in consideration of, for example, the age, weight, sex, difference in diseases, and severity of the condition of individual patients, and the preparation may be administered, for example, in an amount of 0.01 to 100 mg/kg, preferably 0.1 to 50 mg/kg. This dose is administered once a day or divided doses of several times daily.

The compound according to the present invention may be administered in combination with other medicament(s). In this case, the compound according to the present invention may be administered simultaneously with or after or before the administration of other medicament(s). For example, when the subject disease is malignant tumor, the compound according to the present invention can act on target vascular endothelial cells to allow the tumor to regress, followed by the administration of an anti-cancer agent to effectively eliminate the tumor. The type, administration intervals and the like of the anti-cancer agent may be determined depending upon, for example, the type of cancer and the condition of patients. This treatment method can apply to diseases other than the malignant tumor.

According to the present invention, there is provided use of the compound according to the present invention, for the manufacture of a medicament for a disease selected from the group consisting of tumor, diabetic retinopathy, chronic rheumatism, psoriasis, atherosclerosis, and Kaposi's sarcoma.

Further, according to the present invention, there is provided a method for treating a disease selected from the group consisting of tumor, diabetic retinopathy, chronic rheumatism, psoriasis, atherosclerosis, and Kaposi's sarcoma, comprising the step of administering a therapeutically effective amount of the compound according to the present invention, optionally together with a pharmaceutically acceptable carrier, to a mammal, for example, a human.

Furthermore, according to the present invention, there is provided a method for inhibiting the angiogenesis of target blood vessels, comprising the step of bringing the compound according to the present invention into contact with vascular endothelial cells of target blood vessels. Target blood vessels include blood vessels involved in feedings to tissues causative of diseases, for example, tumor tissues, retinopathy tissues, or rheumatism tissues. The compound according to the present invention may be brought into contact with the vascular endothelial cells, for example, by general administration, for example, intravenous administration or oral administration; local administration, for example, percutaneous administration or intraarticular administration; or drug targeting using a carrier, for example, liposome, lipid microsphere, or polymeric forms of drugs.

EXAMPLES

The present invention is further illustrated by the following Examples that are not intended as a limitation of the invention.

Example 1
N-{3-Chloro-4-[(6,7-dimethoxy-4-guinolyl)-oxy]phenyl}-N'-(3-isoxazolyl)urea 3-Chloro-4-[(6,7-dimethoxy-4-quinolyl)oxy]aniline (20 mg) was dissolved in chlorobenzene (2 ml) and N,N-diisopropylethylamine (0.2 ml) to prepare a solution. A solution of triphosgene (18 mg) in chlorobenzene (0.5 ml) was then added to the solution, and the mixture was stirred at room temperature for 30 min. Next, 3-isoxazolamine (10 mg) was added thereto, and the mixture was further stirred at 110° C. overnight. The reaction solution was developed through diatomaceous earth impregnated with a saturated aqueous sodium hydrogencarbonate solution, followed by extraction with chloroform. The solvent in the extract was removed by distillation. The residue was purified by HPLC using chloroform/methanol for development to give the title compound (2 mg, yield 8%).

$^1$H-NMR (CDCl$_3$, 400 MHz): 4.06 (s, 3H), 4.07 (s, 3H), 6.35 (d, J=5.4 Hz, 1H), 6.37 (br, 1H), 7.23 (d, J=8.8 Hz, 1H), 7.45 (s, 1H), 7.51 (dd, J=2.4, 8.8 Hz, 1H), 7.60 (s, 1H), 7.90 (d, J=2.4 Hz, 1H), 8.29 (d, J=2.0 Hz, 1H), 8.49 (d, J=5.4 Hz, 1H)

Mass spectrometry value (ESI-MS, m/z): 441 (M$^+$+1)

Example 2
N-{3-Chloro-4-[(6,7-dimethoxy-4-guinolyl)-oxy]phenyl}-N'-(3-methyl-5-isoxazolyl)urea 3-Chloro-4-[(6,7-dimethoxy-4-quinolyl)oxy]aniline (20 mg) was dissolved in chlorobenzene (2 ml) and N,N-diisopropylethylamine (0.2 ml) to prepare a solution. A solution of triphosgene (18 mg) in chlorobenzene (0.5 ml) was then added to the solution, and the mixture was stirred at room temperature for 30 min. Next, 3-methyl-5-isoxazolamine (12 mg) was added thereto, and the mixture was further stirred at 110° C. overnight. The reaction solution was developed through diatomaceous earth impregnated with a saturated aqueous sodium hydrogencarbonate solution, followed by extraction with chloroform. The solvent in the extract was removed by distillation. The residue was purified by HPLC using chloroform/methanol for development to give the title compound (5 mg, yield 18%).

$^1$H-NMR (CDCl$_3$, 400 MHz): δ 2.28 (s, 3H), 4.03 (s, 3H), 4.06 (s, 3H), 6.09 (s, 1H), 6.33 (d, J=5.4 Hz, !H), 7.17 (d, J=8.8 Hz, 1H), 7.38 (dd, J=2.7, 8.8 Hz, 1H), 7.43 (s, 1H), 7.61 (s, 1H), 7.73 (d, J=2.7 Hz, 1H), 8.47 (d, J=5.4 Hz, 1H), 8.48 (br, 1H)

Mass spectrometry value (ESI-MS, m/z): 455 (M$^+$+1)

Example 3
N-{4-[(6,7-Dimethoxy-4-guinolyl)oxy]-3-fluorophenyl}-N'-(3-isoxazolyl)urea 4-[(6,7-Dimethoxy-4-quinolyl)oxy]-3-fluoroaniline (800 mg) was dissolved in chloroform (20 ml) and triethylamine (1.0 ml) to prepare a solution. A solution of triphosgene (378 mg) in chloroform was then added to the solution, and the mixture was stirred at room temperature for 10 min. Next, 3-aminoisoxazole (252 mg) was added thereto, and the mixture was further stirred at room temperature overnight. Iced water was added to the reaction solution, and the mixture was extracted with chloroform. The organic layer was washed with water and saturated brine and was then dried over anhydrous sodium sulfate. The dried organic layer was filtered and was then concentrated. Ether was added to the residue for crystallization. The crystal was collected by filtration. The collected crystal was purified by chromatography (chloroform:acetone=2:1). A 10% solution of hydrogen chloride in methanol was added to the purification product, followed by concentration. The resultant crystal was washed with ether to give 554 mg of the title compound.

$^1$H-NMR (DMSO-d$_6$, 400 MHz): δ 4.05 (3H, s), 4.06 (3H, s), 6.86 (1H, d, J=1.7 Hz), 6.99 (1H, d, J=6.3 Hz), 7.36 (1H, dd, J=1.5 Hz, J=9.0 Hz), 7.55 (1H, t, J=9.0 Hz), 7.62 (1H, s), 7.78 (1H, s), 7.83 (1H, dd, J=2.4 Hz, J=12.9 Hz), 8.77 (1H, d, J=1.5 Hz), 8.85 (1H, d, J=6.6 Hz), 9.77 (1H, s), 9.96 (1H, s)

Mass spectrometry value (ESI-MS, m/z): 498 (M$^+$+1)

Example 4
N-{2-Chloro-4-[(6,7-dimethoxy-4-guinolyl)-oxy]phenyl}-N'-(5-methyl-3-isoxazolyl)urea 2-Chloro-4-[(6,7-dimethoxy-4-quinolyl)oxy]aniline (100 mg) was dissolved in chloroform (5 ml) and triethylamine (0.5 ml) to prepare a solution. A solution of triphosgene (100 mg) in chloroform was then added to the solution, and the mixture was stirred at room temperature for 15 min. Next, 3-amino-5-methylisoxazole (38 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 78 mg of the title compound.

$^1$H-NMR (CDCl$_3$, 400 MHz): δ 2.42 (3H, s), 4.02 (3H, s), 4.03 (3H, s), 6.00 (1H, br), 6.49 (1H, d, J=5.4 Hz), 7.11 (1H, dd, J=2.7 Hz, J=9.0 Hz), 7.23–7.27 (1H, m), 7.41 (1H, s), 7.49 (1H, s), 8.36 (1H, d, J=9.0 Hz), 8.44 (1H, brs), 8.50 (1H, d, J=5.4 Hz), 9.51 (1H, brs)

Mass spectrometry value (ESI-MS, m/z): 453, 455 (M$^+$−1)

Example 5

N-{2-Cloro-4-[(6,7-dimethoxy-4-guinolyl)-oxy]phenyl}-N'-(3-methyl-5-isoxazolyl)urea 2-Cloro-4-[(6,7-dimethoxy-4-quinolyl)oxy]aniline (100 mg) was dissolved in chloroform (5 ml) and triethylamine (0.5 ml) to prepare a solution. A solution of triphosgene (100 mg) in chloroform was then added to the solution, and the mixture was stirred at room temperature for 15 min. Next, 5-amino-3-methylisoxazole (32 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 53 mg of the title compound.

$^1$H-NMR (CDCl$_3$, 400 MHz): δ 8.46 (1H, d, J=5.1 Hz), 8.23 (1H, d, J=8.8 Hz), 7.70 (1H, s), 7.43 (1H, s), 7.37 (1H, s), 7.15 (1H, d, J=2.7 Hz), 7.07–7.11 (1H, m), 6.43 (1H, d, J=5.1 Hz), 5.99 (1H, s), 3.97 (6H, s), 2.22 (3H, s)

Mass spectrometry value (ESI-MS, m/z): 453 (M$^+$−1)

Example 6

N-{4-[(6,7-Dimethoxy-4-guinolyl)oxy]-2-fluorophenyl}-N'-(3-methyl-5-isoxazolyl)urea 2-Fluoro-4-[(6,7-dimethoxy-4-quinolyl)oxy]aniline (100 mg) was dissolved in chloroform (5 ml) and triethylamine (0.5 ml) to prepare a solution. A solution of triphosgene (100 mg) in chloroform was then added to the solution, and the mixture was stirred at room temperature for 15 min. Next, 5-amino-3-methylisoxazole (37 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 53 mg of the title compound.

$^1$H-NMR (CDCl$_3$, 400 MHz): δ 8.50 (1H, d, J=5.4 Hz), 8.20 (1H, d, d, J=9.0 Hz, J=9.0 Hz), 7.73 (1H, s), 7.49 (1H, s), 7.42 (1H, s), 6.99–7.04 (1H, m), 6.93 (1H, dd, J=2.7 Hz, J=11.2 Hz), 6.50 (1H, d, J=5.4 Hz), 6.05 (1H, s), 4.02 (6H, s), 2.27 (3H, s)

Mass spectrometry value (ESI-MS, m/z): 437 (M$^+$−1)

Example 7

N-{4-[(6,7-Dimethoxy-4-quinolyl)oxy]-3-fluorophenyl}-N'-(3-methyl-5-isoxazolyl)urea 4-[(6,7-Dimethoxy-4-quinolyl)oxy]-3-fluoroaniline (800 mg) was dissolved in chloroform (20 ml) and triethylamine (1.0 ml) to prepare a solution. A solution of triphosgene (378 mg) in chloroform was then added to the solution, and the mixture was stirred at room temperature for 10 min. Next, 5-amino-3-methylisoxazole (294 mg) was added thereto, and the mixture was further stirred at room temperature overnight. Iced water was added to the reaction solution, and the mixture was extracted with chloroform. The organic layer was washed with water and saturated brine and was then dried over anhydrous sodium sulfate. The dried organic layer was filtered and was then concentrated. Ether was added to the residue for crystallization, and the crystal was collected by filtration. The collected crystal was purified by chromatography (chloroform:acetone=2:1). A 10% solution of hydrogen chloride in methanol was added to the purification product, followed by concentration. The resultant crystal was washed with ether to give 669 mg of the title compound.

$^1$H-NMR (DMSO-d$_6$, 400 MHz): δ 2.18 (3H, s), 4.04 (3H, s), 4.05 (3H, s), 5.99 (1H, s), 6.93 (1H, d, J=6.6 Hz), 7.36–7.39 (1H, m), 7.53 (1H, t, J=8.8 Hz), 7.57 (1H, s), 7.75 (1H, s), 7.81 (1H, dd, J=2.7 Hz, J=13.2 Hz), 8.81 (1H, d, J=6.6 Hz), 9.61 (1H, s), 10.44 (1H, s)

Mass spectrometry value (ESI-MS, m/z): 439 (M$^+$+1)

Example 8

N-{4-[(6,7-Dimethoxy-4-guinolyl)oxy]-3-fluorophenyl}-N'-(5-methyl-3-isoxazolyl)urea hydrochloride 4-[(6,7-Dimethoxy-4-quinolyl)oxy]-3-fluoroaniline (800 mg) was dissolved in chloroform (20 ml) and triethylamine (1.0 ml) to prepare a solution. A solution of triphosgene (378 mg) in chloroform was then added to the solution, and the mixture was stirred at room temperature for 10 min. Next, 3-amino-5-methylisoxazole (294 mg) was added thereto, and the mixture was further stirred at room temperature overnight. Iced water was added to the reaction solution, and the mixture was extracted with chloroform. The organic layer was washed with water and saturated brine and was then dried over anhydrous sodium sulfate. The dried organic layer was filtered and was then concentrated. Ether was added to the residue for crystallization, and the crystal was collected by filtration. The collected solid was purified by chromatography (chloroform:acetone=2:1). A 10% solution of hydrogen chloride in methanol was added to the purification product, followed by concentration. The resultant crystal was washed with ether to give 598 mg of the title compound.

$^1$H-NMR (DMSO-d$_6$, 400 MHz): δ 2.38 (3H, s), 4.05 (3H, s), 4.06 (3H, s), 6.56 (1H, s), 7.01 (1H, d, J=6.6 Hz), 7.34–7.37 (1H, m), 7.55 (1H, t, J=9.0 Hz), 7.63 (1H, s), 7.78 (1H, s), 7.83 (1H, dd, J=2.4 Hz, J=13.1 Hz), 8.85 (1H, d, J=6.6 Hz), 9.75 (1H, s), 9.80 (1H, s)

Mass spectrometry value (ESI-MS, m/z): 439 (M$^+$+1)

Example 9

N-{4-[(6,7-Dimethoxy-4-guinolyl)oxy]-2-fluorophenyl}-N'-(5-methyl-3-isoxazolyl)urea 4-[(6,7-Dimethoxy-4-quinolyl)oxy]-2-fluoroaniline (800 mg) was dissolved in chloroform (20 ml) and triethylamine (1.0 ml) to prepare a solution. A solution of triphosgene (378 mg) in chloroform was then added to the solution, and the mixture was stirred at room temperature for 10 min. Next, 3-amino-5-methylisoxazole (270 mg) was added thereto, and the mixture was further stirred at room temperature overnight. Iced water was added to the reaction solution, and the mixture was extracted with chloroform. The organic layer was washed with water and saturated brine and was then dried over anhydrous sodium sulfate. The dried organic layer was filtered and was then concentrated. Ether was added to the residue for crystallization, and the crystal was collected by filtration. The collected crystal was purified by chromatography (chloroform:acetone=2:1) to give 636 mg of the title compound.

$^1$H-NMR (CDCl$_3$, 400 MHz): δ 2.43 (3H, d, J=0.7 Hz), 4.05 (3H, s), 4.05 (3H, s), 5.96 (1H, br), 6.53 (1H, d, J=5.1 Hz), 7.00–7.02 (2H, m), 7.43 (1H, s), 7.51 (1H, s), 8.05 (1H, br), 8.29 (1H, t, J=8.5 Hz), 8.52 (1H, d, J=5.4 Hz), 9.44 (1H, br)

Mass spectrometry value (ESI-MS, m/z): 439 (M$^+$+1)

Example 10

N-{4-[(6,7-Dimethoxy-4-quinazolinyl)oxy]-phenyl}-N'-(5-methyl-3-isoxazolyl)urea

4-[(6,7-Dimethoxy-4-quinazolinyl)oxy]aniline (40 mg) was dissolved in chloroform (1.2 ml) and triethylamine (0.1 ml) to prepare a solution. A solution of triphosgene (20 mg) in chloroform was then added to the solution, and the mixture was stirred at room temperature for 5 min. Next, 3-amino-5-methylisoxazole (15 mg) was added thereto, and the mixture was further stirred at room temperature overnight. Water was added to the reaction solution, and the mixture was subjected to separatory extraction with chloroform. The organic layer was concentrated, and the residue was then purified by chromatography (chloroform:acetone=2:1) to give the title compound (20.0 mg, yield 35.2%).

$^1$H-NMR (DMSO-$d_6$, 400 MHz): δ 2.37 (s, 3H), 3.98 (d, J=5.4 Hz, 6H), 6.55 (s, 1H), 7.24 (d, J=8.8 Hz, 2H), 7.38 (s, 1H), 7.54 (d, J=9.0 Hz, 2H), 7.56 (s, 1H), 8.54 (s, 1H), 9.01 (br, 1H), 9.56 (br, 1H)

Mass spectrometry value (ESI-MS, m/z): 420 ($M^+$−1)

Example 11

N-{4-[(6,7-Dimethoxy-4-quinazolinyl)oxy]-phenyl}-N'-(3-methyl-5-isoxazolyl)urea

4-[(6,7-Dimethoxy-4-quinazolinyl)oxy]aniline (40 mg) was dissolved in chloroform (1.2 ml) and triethylamine (0.1 ml) to prepare a solution. A solution of triphosgene (20 mg) in chloroform was then added to the solution, and the mixture was stirred at room temperature for 5 min. Next, 5-amino-3-methylisoxazole (15 mg) was added thereto, and the mixture was further stirred at room temperature overnight. Water was added to the reaction solution, and the mixture was subjected to separatory extraction with chloroform. The organic layer was concentrated, and the residue was then purified by chromatography (chloroform:acetone=2:1) to give the title compound (9.8 mg, yield 17.3%).

$^1$H-NMR (CDCl$_3$-$d_1$, 400 MHz): δ 2.27 (s, 3H), 4.07 (d, J=2.9 Hz, 6H), 6.04 (s, 1H), 7.24 (d, J=8.8 Hz, 2H), 7.33 (s, 1H), 7.49 (dd, J=2.2 Hz, 9.0 Hz, 2H), 7.55 (s, 1H), 8.61 (s, 1H)

Mass spectrometry value (ESI-MS, m/z): 420 ($M^+$−1)

Example 12

N-{2-Chloro-4-[(6,7-dimethoxy-4-quinazolinyl)oxy]phenyl}-N'-(5-methyl-3-isoxazolyl)urea 2-Chloro-4-[(6,7-dimethoxy-4-quinazolinyl)oxy]-aniline (43 mg) was dissolved in chloroform (1.2 ml) and triethylamine (0.1 ml) to prepare a solution. A solution of triphosgene (20 mg) in chloroform was then added to the solution, and the mixture was stirred at room temperature for 5 min. Next, 3-amino-5-methylisoxazole (15 mg) was added thereto, and the mixture was further stirred at room temperature overnight. Water was added to the reaction solution, and the mixture was subjected to separatory extraction with chloroform. The organic layer was concentrated, and the residue was then purified by chromatography (chloroform:acetone=2:1) to give the title compound (19.0 mg, yield 32%).

$^1$H-NMR (DMSO-$d_6$, 400 MHz): δ 2.37 (s, 3H), 3.98 (d, J=6.8 Hz, 6H), 6.51 (s, 1H), 7.32 (dd, J=2.7 Hz, 9.0 Hz, 1H), 7.39 (s, 1H), 7.55 (s, 1H), 7.57 (d, J=2.7 Hz, 1H), 8.20 (dd, J=2.69, 9.0 Hz, 1H), 8.56 (s, 1H), 8.75 (br, 1H), 10.14 (br, 1H)

Mass spectrometry value (ESI-MS, m/z): 454 ($M^+$−1)

Example 13

N-{2-Chloro-4-[(6,7-dimethoxy-4-quinazolinyl)oxy]phenyl}-N'-(3-methyl-5-isoxazolyl)urea 2-Chloro-4-[(6,7-dimethoxy-4-quinazolinyl)oxy]-aniline (43 mg) was dissolved in chloroform (1.2 ml) and triethylamine (0.1 ml) to prepare a solution. A solution of triphosgene (20 mg) in chloroform was then added to the solution, and the mixture was stirred at room temperature for 5 min. Next, 5-amino-3-methylisoxazole (15 mg) was added thereto, and the mixture was further stirred at room temperature overnight. Water was added to the reaction solution, and the mixture was subjected to separatory extraction with chloroform. The organic layer was concentrated, and the residue was then purified by chromatography (chloroform:acetone=2:1) to give the title compound (18.1 mg, yield 31%).

$^1$H-NMR (DMSO-$d_6$, 400 MHz): δ 2.18 (s, 3H), 3.98 (d, J=6.8 Hz, 6H), 5.98 (s, 1H), 7.33 (dd, J=2.4, 9.0 Hz, 1H), 7.40 (s, 1H), 7.55 (s, 1H), 7.58 (d, J=2.7 Hz, 1H), 8.17 (dd, J=3.9, 9.0 Hz, 1H), 8.57 (s, 1H)

Mass spectrometry value (ESI-MS, m/z): 454 ($M^+$−1)

Example 14

N-{3-Chloro-4-[(6,7-dimethoxy-4-quinazolinyl)oxy]phenyl}-N'-(5-methyl-3-isoxazolyl)urea 3-Chloro-4-[(6,7-dimethoxy-4-quinazolinyl)oxy]-aniline (42 mg) was dissolved in chloroform (2.0 ml) and triethylamine (0.13 ml) to prepare a solution. A solution of triphosgene (19 mg) in chloroform was then added to the solution, and the mixture was stirred at room temperature for 5 min. Next, 3-amino-5-methylisoxazole (14 mg) was added thereto, and the mixture was further stirred at room temperature overnight. Water was added to the reaction solution, and the mixture was subjected to separatory extraction with chloroform. The organic layer was concentrated and was evaporated to dryness. Diethyl ether was added to the resultant solid, and the solution was filtered. The filtrate was concentrated, and methyl alcohol was added to the residue. The resultant crystal was collected by filtration to give the title compound (8.8 mg, yield 15%).

$^1$H-NMR (DMSO-$d_6$, 400 MHz): δ 2.38 (s, 3H), 3.99 (d, J=5.9 Hz, 6H), 6.55 (s, 1H), 7.40–7.42 (m, 3H), 7.57 (s, 1H), 7.84–7.86 (m, 1H), 8.55 (s, 1H), 9.08 (br, 1H), 9.60 (br, 1H)

Mass spectrometry value (ESI-MS, m/z): 454 ($M^+$−1)

Example 15

N-{3-Chloro-4-[(6,7-dimethoxy-4-quinazolinyl)oxy]phenyl}-N'-(3-methyl-5-isoxazolyl)urea 3-Chloro-4-[(6,7-dimethoxy-4-quinazolinyl)oxy]-aniline (84 mg) was dissolved in chloroform (2.5 ml) and triethylamine (0.25 ml) to prepare a solution. A solution of triphosgene (38 mg) in chloroform was then added to the solution, and the mixture was stirred at room temperature for 5 min. Next, 5-amino-3-methylisoxazole (27 mg) was added thereto, and the mixture was further stirred at room temperature overnight. Water was added to the reaction solution, and the mixture was subjected to separatory extraction with chloroform. The organic layer was concentrated and was evaporated to dryness. Diethyl ether was added to the resultant solid, and the solid was collected by filtration and was further washed with methyl alcohol to give the title compound (34.2 mg, yield 30%).

$^1$H-NMR (DMSO-$d_6$, 400 MHz): δ 2.18 (s, 3H), 3.99 (d, J=5.9 Hz, 6H), 5.99 (s, 1H), 7.41 (s, 1H), 7.42–7.45 (m, 2H), 7.57 (s, 1H), 7.84–7.86 (m, 1H), 8.54 (s, 1H), 9.17 (br, 1H), 10.31 (br, 1H)

Mass spectrometry value (ESI-MS, m/z): 454 ($M^+$−1)

Example 16

N-{4-[(6,7-Dimethoxy-4-quinazolinyl)oxy]-phenyl}-N'-(3-methyl-5-isothiazolyl)urea 4-[(6,7-Dimethoxy-4-quinazolinyl)oxy]aniline (40 mg) was dissolved in chloroform (1.2 ml) and triethylamine (0.2 ml) to prepare a solution. A solution of triphosgene (20 mg) in chloroform was then added to the solution, and the mixture was stirred at room temperature for 5 min. Next, 5-amino-3-methylisothiazole hydrochloride (22 mg) was added thereto, and the mixture was further stirred at room temperature overnight. Water was added to the reaction solution, and the mixture was subjected to separatory extraction with chloroform. The organic layer was concentrated, and the residue was then purified by chromatography (chloroform:acetone=2:1) to give the title compound (17.5 mg, yield 29.7%).

$^1$H-NMR (CDCl$_3$, 400 MHz): δ 2.38 (s, 3H), 4.07 (d, J=4.4 Hz, 6H), 6.40 (s, 1H), 7.21–7.25 (m, 2H), 7.33 (s, 1H), 7.47 (d, J=8.8 Hz, 2H), 7.55 (s, 1H), 8.60 (s, 1H)

Mass spectrometry value (ESI-MS, m/z): 436 (M$^+$−1)

Example 17

N-{2-Chloro-4-[(6,7-dimethoxy-4-quinazolinyl)oxy]phenyl}-N'-(3-methyl-5-isothiazolyl)urea 2-Chloro-4-[(6,7-dimethoxy-4-quinazolinyl)oxy]-aniline (43 mg) was dissolved in chloroform (1.2 ml) and triethylamine (0.2 ml) to prepare a solution. A solution of triphosgene (20 mg) in chloroform was then added to the solution, and the mixture was stirred at room temperature for 5 min. Next, 5-amino-3-methylisothiazole hydrochloride (22 mg) was added thereto, and the mixture was further stirred at room temperature overnight. Water was added to the reaction solution, and the mixture was subjected to separatory extraction with chloroform. The organic layer was concentrated, and the residue was then purified by chromatography (chloroform:acetone=2:1) to give the title compound (13.7 mg, yield 22%).

$^1$H-NMR (DMSO-d$_6$, 400 MHz): δ 2.30 (s, 3H), 3.99 (d, J=6.6 Hz, 6H), 6.68 (s, 1H), 7.34 (dd, J=2.7, 9.0 Hz, 1H), 7.40 (s, 1H), 7.56 (s, 1H), 7.59 (d, J=2.7 Hz, 1H), 8.13–8.17 (m, 1H), 8.57 (s, 1H), 8.77 (br, 1H), 10.94 (br, 1H)

Mass spectrometry value (ESI-MS, m/z): 470 (M$^+$−1)

Example 18

N-{3-Chloro-4-[(6,7-dimethoxy-4-quinazolinyl)oxy]phenyl}-N'-(3-methyl-5-isothiazolyl)urea 3-Chloro-4-[(6,7-dimethoxy-4-quinazolinyl)oxy]-aniline (84 mg) was dissolved in chloroform (2.5 ml) and triethylamine (0.50 ml) to prepare a solution. A solution of triphosgene (38 mg) in chloroform was then added to the solution, and the mixture was stirred at room temperature for 5 min. Next, 5-amino-3-methylisothiazole (38 mg) was added thereto, and the mixture was further stirred at room temperature overnight. Water was added to the reaction solution, and the mixture was subjected to separatory extraction with chloroform. The organic layer was concentrated and was evaporated to dryness. Diethyl ether was added to the residue, and the solid was collected by filtration and was washed with methyl alcohol to give the title compound (32.2 mg, yield 27%).

$^1$H-NMR (DMSO-d$_6$, 400 MHz): δ 2.30 (s, 3H), 3.99 (d, J=5.61 Hz, 6H), 6.68 (s, 1H), 7.41 (s, 1H), 7.44 (s, 1H), 7.48 (dd, J=2.4 Hz, 8.8 Hz, 1H), 7.58 (s, 1H), 7.85 (d, J=2.4 Hz, 1H), 8.55 (s, 1H), 9.46 (br, 1H), 10.59 (br, 1H)

Mass spectrometry value (ESI-MS, m/z): 470 (M$^+$−1)

Example 19

N-{3-Chloro-4-[(6,7-dimethoxy-4-quinolyl)-oxy]phenyl}-N'-(1H-5-pyrazolyl)urea

3-Chloro-4-[(6,7-dimethoxy-4-quinolyl)oxy]aniline (20 mg) was dissolved in chlorobenzene (2 ml) and N,N-diisopropylethylamine (0.2 ml) to prepare a solution. A solution of triphosgene (18 mg) in chlorobenzene (0.5 ml) was then added to the solution, and the mixture was stirred at room temperature for 30 min. Next, 1H-5-pyrazolamine (10 mg) was added thereto, and the mixture was further stirred at 110° C. overnight. The reaction solution was developed through diatomaceous earth impregnated with a saturated aqueous sodium hydrogencarbonate solution, followed by extraction with chloroform. The solvent in the extract was removed by distillation. The residue was purified by HPLC using chloroform/methanol for development to give the title compound (1 mg, yield 4%).

$^1$H-NMR (CDCl$_3$, 400 MHz): δ 4.05 (S, 3H), 4.07 (s, 3H), 5.93 (d, J=2.4 Hz, 1H), 6.34 (d, J=5.1 Hz, 1H), 7.20 (d, J=8.8 Hz, 1H), 7.43 (s, 1H), 7.52 (d, J=2.4 Hz, 1H), 7.55 (dd, J=2.7 Hz, 8.8 Hz, 1H), 7.61 (s, 1H), 7.86 (d, J=2.4 Hz, 1H), 8.48 (d, J=5.4 Hz, 1H)

Mass spectrometry value (ESI-MS, m/z): 440 (M$^+$+1)

Example 20

N-{4-[(6,7-Dimethoxy-4-quinolyl)oxy]-2-fluorophenyl}-N'-(1H-5-pyrazolyl)urea

4-[(6,7-Dimethoxy-4-quinolyl)oxy]-2-fluoroaniline (20 mg) was dissolved in chlorobenzene (1.5 ml) and N,N-diisopropylethylamine (0.15 ml) to prepare a solution. A solution of triphosgene (19 mg) in chlorobenzene (0.5 ml) was then added to the solution, and the mixture was stirred at room temperature for 30 min. Next, 1H-5-pyrazolamine (10 mg) was added thereto, and the mixture was further stirred at 100° C. overnight. The reaction solution was developed through diatomaceous earth impregnated with a saturated aqueous sodium hydrogencarbonate solution, followed by extraction with chloroform. The solvent in the extract was removed by distillation. The residue was purified by HPLC using chloroform/methanol for development to give the title compound (3 mg, yield 11%).

Mass spectrometry value (ESI-MS, m/z): 424 (M$^+$+1)

Example 21

N-{4-[(6,7-Dimethoxy-4-quinolyl)oxy]-2-fluorophenyl}-N'-(5-methyl-1,3-thiazol-2-yl)urea hydrochloride 4-[(6,7-Dimethoxy-4-quinolyl)oxy]-2-fluoroaniline (300 mg) was dissolved in chloroform (6 ml) and triethylamine (0.3 ml) to prepare a solution. A solution of triphosgene (142 mg) in chloroform was then added to the solution, and the mixture was stirred at room temperature for 10 min. Next, 2-amino-5-methylthiazole (119 mg) was added thereto, and the mixture was further stirred at room temperature overnight. Iced water was added to the reaction solution, and the mixture was extracted with chloroform. The organic layer was washed with water and saturated brine and was then dried over anhydrous sodium sulfate. The dried organic layer was filtered and was then concentrated. Ether was added to the residue for crystallization, and the crystal was collected by filtration. The crystal was purified by chromatography (chloroform:acetone=2:1). A 10% hydrogen chloride-methanol solution was added to the purified crystal, and the solution was then concentrated. The resultant crystal was washed with ether to give 380 mg of the title compound.

$^1$H-NMR (CDCl$_3$, 400 MHz): δ 2.47 (3H, d, J=1.5 Hz), 4.11 (3H, s), 4.19 (3H, s), 6.82 (1H, d, J=6.6 Hz), 7.08–7.15 (2H, m), 7.16 (1H, d, J=1.5 Hz), 7.63 (1H, s), 8.03 (1H, s), 8.27 (1H, t, J=8.5 Hz), 8.63 (1H, d, J=6.6 Hz)

Mass spectrometry value (ESI-MS, m/z): 453 (M$^+$−1)

Example 22
N-{2-Chloro-4-[(6,7-dimethoxy-4-guinolyl)-oxy]phenyl}-N'-(4-methyl-1,3-thiazol-2-yl)urea 2-Chloro-4-[(6,7-dimethoxy-4-quinolyl)oxy]aniline (100 mg) was dissolved in chloroform (10 ml) and pyridine (0.1 ml) to prepare a solution. A solution of triphosgene (45 mg) in chloroform was then added to the solution, and the mixture was stirred at room temperature for 10 min. Next, 2-amino-4-methylthiazole (38 mg) was added thereto, and the mixture was further stirred at room temperature overnight. Iced water was added to the reaction solution, and the mixture was extracted with chloroform. The organic layer was washed with water and saturated brine and was then dried over anhydrous sodium sulfate. The dried organic layer was filtered and was then concentrated. Ether was added to the residue for crystallization, and the crystal was collected by filtration. The crystal was purified by chromatography (chloroform:acetone=2:1) to give 90 mg of the title compound.

$^1$H-NMR (CDCl$_3$, 400 MHz): δ 2.40 (3H, d, J=0.7 Hz), 4.05 (3H, s), 4.05 (3H, s), 6.44 (1H, d, J=1.0 Hz), 6.51 (1H, d, J=5.1 Hz), 7.15 (1H, dd, J=2.7 Hz, J=9.0 Hz), 7.28 (1H, d, J=2.7 Hz), 7.43 (1H, s), 7.52 (1H, s), 8.50 (1H, d, J=9.0 Hz), 8.52 (1H, d, J=5.1 Hz)

Mass spectrometry value (ESI-MS, m/z): 469 (M$^+$−1)

Example 23
N-{4-[(6,7-Dimethoxy-4-guinolyl)oxy]-2-fluorophenyl}-N'-(4,5-dimethyl-1,3-thiazol-2-yl)urea 4-[(6,7-Dimethoxy-4-quinolyl)oxy]-2-fluoroaniline (95 mg) was dissolved in chloroform (3 ml) and pyridine (0.2 ml) to prepare a solution. A solution of triphosgene (45 mg) in chloroform was then added to the solution, and the mixture was stirred at room temperature for 10 min. Next, 2-amino-4,5-dimethylthiazole hydrochloride (54 mg) was added thereto, and the mixture was further stirred at room temperature overnight. Iced water was added to the reaction solution, and the mixture was extracted with chloroform. The organic layer was washed with water and saturated brine and was then dried over anhydrous sodium sulfate. The dried organic layer was filtered and was then concentrated. Ether was added to the residue for crystallization, and the crystal was collected by filtration. The crystal was purified by chromatography (chloroform:acetone=2:1) to give 29 mg of the title compound.

$^1$H-NMR (CDCl$_3$, 400 MHz): δ 2.27 (3H, s), 2.28 (3H, s), 4.04 (3H, s), 4.05 (3H, s), 6.51 (1H, d, J=5.4 Hz), 6.97–7.02 (2H, m), 7.43 (1H, s), 7.51 (1H, s), 8.39 (1H, t, J=8.8 Hz), 8.51 (1H, d, J=5.4 Hz)

Mass spectrometry value (ESI-MS, m/z): 469 (M$^+$+1)

Example 24
N-{2-Chloro-4-[(6,7-dimethoxy-4-guinolyl)oxy]phenyl}-N'-(4,5-dimethyl-1,3-thiazol-2-yl)urea 2-Chloro-4-[(6,7-dimethoxy-4-quinolyl)oxy]aniline (100 mg) was dissolved in chloroform (5 ml) and triethylamine (0.5 ml) to prepare a solution. A solution of triphosgene (100 mg) in chloroform was then added to the solution, and the mixture was stirred at room temperature for 15 min. Next, 2-amino-4,5-dimethylthiazole hydrochloride (55 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 62 mg of the title compound.

$^1$H-NMR (CDCl$_3$, 400 MHz): δ 8.49 (1H, d, J=5.2 Hz), 8.46 (1H, d, J=9.0 Hz), 7.50 (1H, s), 7.41 (1H, s), 7.24–7.26 (1H, m), 7.11 (1H, dd, J=2.7 Hz, J=9.0 Hz), 6.48 (1H, d, J=5.1 Hz), 4.03 (3H, s), 4.03 (3H, s), 2.26 (3H, s), 2.24 (3H, s)

Mass spectrometry value (ESI-MS, m/z): 483, 485 (M$^+$−1)

Example 25
N-{3-Chloro-4-[(6,7-dimethoxy-4-guinolyl)oxy]phenyl}-N'-(4,5-dimethyl-1,3-thiazol-2-yl)urea 3-Chloro-4-[(6,7-dimethoxy-4-quinolyl)oxy]aniline (100 mg) was dissolved in chloroform (5 ml) and triethylamine (0.5 ml) to prepare a solution. A solution of triphosgene (100 mg) in chloroform was then added thereto, and the mixture was stirred at room temperature for 15 min. Next, 2-amino-4,5-dimethylthiazole hydrochloride (55 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 29 mg of the title compound.

$^1$H-NMR (CDCl$_3$, 400 MHz): δ 8.46 (1H, d, J=5.4 Hz), 7.88 (1H, d, J=2.4 Hz), 7.59 (1H, s), 7.48 (1H, dd, J=2.4 Hz, J=8.8 Hz), 7.43 (1H, s), 7.23–7.26 (1H, m), 7.17 (1H, d, J=8.8 Hz), 6.31 (1H, d, J=5.4 Hz), 4.05 (3H, s), 4.03 (3H, s), 2.25 (3H, s), 2.19 (3H, s)

Mass spectrometry value (ESI-MS, m/z): 483, 485 (M$^+$−1)

Example 26
N-[4-[(6,7-Dimethoxy-4-guinolyl)oxy]-2-(trifluoromethyl)phenyl]-N'-(4,5-dimethyl-1,3-thiazol-2-yl)urea 4-[(6,7-Dimethoxy-4-quinolyl)oxy]-2-(trifluoromethyl)aniline (100 mg) was dissolved in chloroform (5 ml) and triethylamine (0.5 ml) to prepare a solution. A solution of triphosgene (100 mg) in chloroform was then added to the solution, and the mixture was stirred at room temperature for 15 min. Next, 2-amino-4,5-dimethylthiazole hydrochloride (55 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 43 mg of the title compound.

$^1$H-NMR (CDCl$_3$, 400 MHz): δ 8.50 (1H, d, J=5.4 Hz), 8.26 (1H, d, J=8.6 Hz), 7.50 (1H, s), 7.42–7.46 (2H, m), 7.35 (1H, dd, J=3.0 Hz, J=9.0 Hz), 6.48 (1H, d, J=5.4 Hz), 4.04 (3H, s), 4.03 (3H, s), 2.25 (3H, s), 2.21 (3H, s)

Mass spectrometry value (ESI-MS, m/z): 517 (M$^+$−1)

Example 27
N-{4-[(6,7-Dimethoxy-4-guinolyl)oxy]-2-fluorophenyl}-N'-(1,3-thiazol-2-yl)urea hydrochloride 4-[(6,7-Dimethoxy-4-quinolyl)oxy]-2-fluoroaniline (12 g) was dissolved in chloroform (350 ml) and triethylamine (50 ml) to prepare a solution. A solution of triphosgene (12 g) in chloroform was then added to the solution, and the mixture was stirred at room temperature for 30 min. Next, 2-aminothiazole (4.77 g) was added thereto, and the mixture was further stirred at room temperature overnight. Iced water was added to the reaction solution, and the mixture was extracted with chloroform. The organic layer was washed with water and saturated brine and was then dried over anhydrous magnesium sulfate. The dried organic layer was filtered and was then concentrated, and ether was added to the residue for crystallization, followed by collection of the resultant crystal by filtration. The crystal was further washed with methanol and was collected by filtration. A 10% hydrogen chloride-methanol solution was added to the collected crystal, and the solution was concentrated. The resultant crystal was washed with a mixed solution composed of ether and ethanol to give 11.5 g of the title compound.

$^1$H-NMR (DMSO-$d_6$, 400 MHz): δ 4.04 (s, 3H), 4.05 (s, 3H), 7.00 (d, J=6.8 Hz, 1H), 7.17 (d, J=3.7 Hz, 1H), 7.27–7.32 (m, 1H), 7.41 (d, J=3.7 Hz, 1H), 7.55–7.60 (m, 1H), 7.67 (s, 1H), 7.77 (s, 1H), 8.30–8.37 (m, 1H), 8.85 (d, J=6.6 Hz, 1H), 9.35 (brs, 1H)

Mass spectrometry value (ESI-MS, m/z): 441 ($M^+$+1)

Example 28

N-{4-[(6,7-Dimethoxy-4-quinolyl)oxy]-2-fluorophenyl}-N'-(4-methyl-1,3-thiazol-2-yl)urea hydrochloride 4-[(6,7-Dimethoxy-4-quinolyl)oxy]-2-fluoroaniline (10 g) was dissolved in chloroform (300 ml) and triethylamine (40 ml) to prepare a solution. A solution of triphosgene (10 g) in chloroform was then added to the solution, and the mixture was stirred at room temperature for 30 min. Next, 2-amino-4-methylthiazole (4.36 g) was added thereto, and the mixture was further stirred at room temperature overnight. Iced water was added to the reaction solution, and the mixture was extracted with chloroform. The organic layer was washed with water and saturated brine and was then dried over anhydrous magnesium sulfate. The dried organic layer was filtered and was then concentrated, and ether was added to the residue for crystallization, followed by collection of the resultant crystal by filtration. The crystal was purified by chromatography (chloroform:acetone=2:1). A 10% solution of hydrogen chloride in methanol was added to the purification product, followed by concentration. The resultant crystal was washed with ether to give 6.0 g of the title compound.

$^1$H-NMR (DMSO-$d_6$, 400 MHz): δ 2.24 (s, 3H), 4.04 (s, 3H), 4.05 (s, 3H), 6.71 (s, 1H), 7.00 (d, J=6.8 Hz, 1H), 7.26–7.31 (m, 1H), 7.55–7.60 (m, 1H), 7.68 (s, 1H), 7.76 (s, 1H), 8.29–8.36 (m, 1H), 8.84 (d, J=6.8 Hz, 1H)

Mass spectrometry value (ESI-MS, m/z): 455 ($M^+$+1)

Example 29

Ethyl 2-{2-[({4-[(6,7-dimethoxy-4-quinolyl)oxy]-2-fluoroanilino}carbonyl)amino]-1,3-thiazol-4-yl}acetate 4-[(6,7-Dimethoxy-4-quinolyl)oxy]-2-fluoroaniline (30 mg) was dissolved in chloroform (3 ml) to prepare a solution. Triethylamine (0.3 ml) and a solution of triphosgene (27 mg) in chloroform (0.2 ml) were then added to the solution, and the mixture was stirred at room temperature for 30 min. Next, a solution of ethyl (2-amino-4-thiazolyl) acetate (76 mg) in chloroform (0.6 ml) was added thereto, and the mixture was further stirred at room temperature overnight. Water was added to the reaction solution, and the mixture was subjected to separatory extraction with chloroform. The extract was washed with saturated brine and was dried over anhydrous sodium sulfate. The organic layer was concentrated under the reduced pressure, and the residue was purified by chromatography on silica gel using chloroform/acetone for development to give 22 mg of the title compound.

$^1$H-NMR (CDCl$_3$, 400 MHz): δ 1.29 (t, 3H, J=7.1 Hz), 3.76 (s, 2H), 4.04 (s, 3H), 4.05 (s, 3H), 4.23 (q, 2H, J=7.1 Hz), 6.73 (s, 1H), 6.52 (d, 1H, J=5.4 Hz), 6.97–7.02 (m, 2H), 7.44 (s, 1H), 7.51 (s, 1H), 8.35 (t, 1H, J=9.0 Hz), 8.52 (d, 1H, J=5.4 Hz)

Mass spectrometry value (ESI-MS, m/z): 525 ($M^+$−1)

Example 30

N-[4-(Tert-butyl)-1,3-thiazol-2-yl]-N'-{4-[(6,7-dimethoxy-4-quinolyl)oxy]-2-fluorophenyl}urea 4-[(6,7-Dimethoxy-4-quinolyl)oxy]-2-fluoroaniline (30 mg) was dissolved in chloroform (3 ml) to prepare a solution. Triethylamine (0.3 ml) and a solution of triphosgene (27 mg) in chloroform (0.2 ml) were then added to the solution, and the mixture was stirred at room temperature for 30 min. Next, a solution of 2-amino-4-t-butylthiazole (64 mg) in chloroform (0.6 ml) was added thereto, and the mixture was further stirred at room temperature overnight. Water was added to the reaction solution, and the mixture was subjected to separatory extraction with chloroform. The extract was washed with saturated brine and was dried over anhydrous sodium sulfate. The organic layer was concentrated under the reduced pressure, and the residue was purified by chromatography on silica gel using chloroform/acetone for development to give 26 mg of the title compound.

$^1$H-NMR (CDCl$_3$, 400 MHz): δ 1.36 (s, 9H), 4.06 (s, 3H), 4.06 (s, 3H), 6.41 (s, 1H), 6.54 (d, 1H, J=5.4 Hz), 7.00–7.04 (m, 2H), 7.45 (s, 1H), 7.53 (s, 1H), 8.48 (t, 1H, J=8.5 Hz), 8.53 (d, 1H, J=5.1 Hz)

Mass spectrometry value (ESI-MS, m/z): 495 ($M^+$−1)

Example 31

Ethyl 2-{2-[({2-chloro-4-[(6,7-dimethoxy-4-quinolyl)oxy]anilino}carbonyl)amino]-1,3-thiazol-4-yl}acetate 2-Chloro-4-[(6,7-dimethoxy-4-quinolyl)oxy]aniline (30 mg) was dissolved in chloroform (3 ml) to prepare a solution. Triethylamine (0.3 ml) and a solution of triphosgene (27 mg) in chloroform (0.2 ml) were then added thereto, and the mixture was stirred at room temperature for 30 min. Next, a solution of ethyl (2-amino-4-thiazolyl) acetate (76 mg) in chloroform (0.6 ml) was added thereto, and the mixture was further stirred at room temperature overnight. Water was added to the reaction solution, and the mixture was subjected to separatory extraction with chloroform. The extract was washed with saturated brine and was dried over anhydrous sodium sulfate. The organic layer was concentrated under the reduced pressure, and the residue was purified by chromatography on silica gel using chloroform/acetone for development to give 23 mg of the title compound.

$^1$H-NMR (CDCl$_3$, 400 MHz): δ 1.23 (t, 3H, J=7.1 Hz), 3.76 (s, 2H), 4.05 (s, 3H), 4.05 (s, 3H), 4.21 (q, 2H, J=7.1 Hz), 6.51 (d, 1H, J=5.4 Hz), 6.75 (s, 1H), 7.14 (dd, 1H, J=2.7 Hz, J=9.0 Hz), 7.27 (d, 1H, J=2.7 Hz), 7.44 (s, 1H), 7.51 (s, 1H), 8.46 (d, 1H, J=9.0 Hz), 8.52 (d, 1H, J=5.4 Hz)

Mass spectrometry value (ESI-MS, m/z): 541 ($M^+$−1)

Example 32

N-(5-Bromo-1,3-thiazol-2-yl)-N'-{2-chloro-4-[(6,7-dimethoxy-4-quinolyl)oxy]phenyl}urea 2-Chloro-4-[(6,7-dimethoxy-4-quinolyl)oxy]aniline (30 mg) was dissolved in chloroform (3 ml) to prepare a solution. Triethylamine (0.3 ml) and a solution of triphosgene (27 mg) in chloroform (0.2 ml) were then added thereto, and the mixture was stirred at room temperature for 30 min. Next, a solution of 2-amino-5-bromothiazole bromate (106 mg) in chloroform (0.6 ml) was added thereto, and the mixture was further stirred at room temperature overnight. Water was added to the reaction solution, and the mixture was subjected to separatory extraction with chloroform. The extract was washed with saturated brine and was dried over anhydrous sodium sulfate. The organic layer was concentrated under the reduced pressure, and the residue was purified by chromatography on silica gel using chloroform/acetone for development to give 6 mg of the title compound.

$^1$H-NMR (CDCl$_3$, 400 MHz): 4.04 (s, 3H), 4.04 (s, 3H), 6.48 (d, 1H, J=5.4 Hz), 7.16 (dd, 1H, J=2.7 Hz, J=9.0 Hz), 7.26 (d, 1H, J=2.7 Hz), 7.35 (s, 1H), 7.43 (s, 1H), 7.50 (s, 1H), 8.41 (d, 1H, J=9.0 Hz), 8.51 (d, 1H, J=5.4 Hz)

Mass spectrometry value (ESI-MS, m/z): 534 (M$^+$−1)

Example 33

N-[4-(Tert-butyl)-1,3-thiazol-2-yl]-N'-{2-chloro-4-[(6,7-dimethoxy-4-guinolyl)oxy]phenyl}urea 2-Chloro-4-[(6,7-dimethoxy-4-quinolyl)oxy]aniline (30 mg) was dissolved in chloroform (3 ml) to prepare a solution. Triethylamine (0.3 ml) and a solution of triphosgene (27 mg) in chloroform (0.2 ml) were then added thereto, and the mixture was stirred at room temperature for 30 min. Next, a solution of 2-amino-4-t-butylthiazole (64 mg) in chloroform (0.6 ml) was added thereto, and the mixture was further stirred at room temperature overnight. Water was added to the reaction solution, and the mixture was subjected to separatory extraction with chloroform. The extract was washed with saturated brine and was dried over anhydrous sodium sulfate. The organic layer was concentrated under the reduced pressure, and the residue was purified by chromatography on silica gel using chloroform/acetone for development to give 14 mg of the title compound.

$^1$H-NMR (CDCl$_3$, 400 MHz): δ 1.36 (s, 9H), 4.05 (s, 3H), 4.06 (s, 3H), 6.42 (s, 1H), 6.54 (d, 1H, J=5.1 Hz), 7.15 (dd, 1H, J=2.7 Hz, J=9.0 Hz), 7.28 (d, 1H, J=2.7 Hz), 7.45 (s, 1H), 7.52 (s, 1H), 8.40 (d, 1H, J=9.0 Hz), 8.53 (d, 1H, J=5.1 Hz)

Mass spectrometry value (ESI-MS, m/z): 511 (M$^+$−1)

Example 34

N-{2-Chloro-4-[(6,7-dimethoxy-4-guinolyl)oxy]phenyl}-N'-(5-chloro-1,3-thiazol-2-yl)urea 2-Chloro-4-[(6,7-dimethoxy-4-quinolyl)oxy]aniline (30 mg) was dissolved in chloroform (3 ml) to prepare a solution. Triethylamine (0.3 ml) and a solution of triphosgene (27 mg) in chloroform (0.2 ml) were then added to the solution, and the mixture was stirred at room temperature for 30 min. Next, a solution of 2-amino-5-chlorothiazole (70 mg) in chloroform (0.6 ml) was added thereto, and the mixture was further stirred at room temperature overnight. Water was added to the reaction solution, and the mixture was subjected to separatory extraction with chloroform. The extract was washed with saturated brine and was dried over anhydrous sodium sulfate. The organic layer was concentrated under the reduced pressure, and the residue was purified by chromatography on silica gel using chloroform/ acetone for development to give 6 mg of the title compound.

$^1$H-NMR (CDCl$_3$, 400 MHz): 4.04 (s, 3H), 4.05 (s, 3H), 6.50 (d, 1H, J=5.4 Hz), 7.15 (dd, 1H, J=2.7 Hz, J=9.0 Hz), 7.26–7.27 (m, 2H), 7.44 (s, 1H), 7.50 (s, 1H), 8.38 (t, 1H, J=9.0 Hz), 8.52 (d, 1H, J=5.4 Hz)

Mass spectrometry value (ESI-MS, m/z): 489, 491 (M$^+$−1)

Example 35

N-(5-Bromo-1,3-thiazol-2-yl)-N'-{4-[(6,7-dimethoxy-4-guinolyl)oxy]-2-fluorophenyl}urea 4-[(6,7-Dimethoxy-4-quinolyl)oxy]-2-fluoroaniline (30 mg) was dissolved in chloroform (3 ml) to prepare a solution. Triethylamine (0.3 ml) and a solution of triphosgene (27 mg) in chloroform (0.2 ml) were then added to the solution, and the mixture was stirred at room temperature for 30 min. Next, a solution of 2-amino-5-bromothiazole bromate (106 mg) in chloroform (0.6 ml) was added thereto, and the mixture was further stirred at room temperature overnight. Water was added to the reaction solution, and the mixture was subjected to separatory extraction with chloroform. The extract was washed with saturated brine and was dried over anhydrous sodium sulfate. The organic layer was concentrated under the reduced pressure, and the residue was purified by chromatography on silica gel using chloroform/acetone for development to give 5 mg of the title compound.

$^1$H-NMR (CDCl$_3$, 400 MHz): 3.93 (s, 3H), 3.95 (s, 3H), 6.56 (d, 1H, J=5.1 Hz), 7.13 (d, 1H, J=7.8 Hz), 7.37–7.49 (m, 4H), 8.16 (t, 1H, J=9.3 Hz), 8.50 (d, 1H, J=4.9 Hz), 8.99 (br, 1H), 11.02 (br, 1H)

Mass spectrometry value (ESI-MS, m/z): 518, 520 (M$^+$−1)

Example 36

N-(5-Acetyl-4-methyl-1,3-thiazol-2-yl)-N'-{4-[(6,7-dimethoxy-4-quinolyl)oxy]-2-fluorophenyl}urea 4-[(6,7-Dimethoxy-4-quinolyl)oxy]-2-fluoroaniline (30 mg) was dissolved in chloroform (3 ml) to prepare a solution. Triethylamine (0.3 ml) and a solution of triphosgene (27 mg) in chloroform (0.2 ml) were then added thereto, and the mixture was stirred at room temperature for 30 min. Next, a solution of 5-acetyl-2-amino-4-methylthiazole (64 mg) in chloroform (0.6 ml) was added thereto, and the mixture was further stirred at room temperature overnight. Water was added to the reaction solution, and the mixture was subjected to separatory extraction with chloroform. The extract was washed with saturated brine and was dried over anhydrous sodium sulfate. The organic layer was concentrated under the reduced pressure, and the residue was purified by chromatography on silica gel using chloroform/acetone for development to give 6 mg of the title compound.

$^1$H-NMR (CDCl$_3$, 400 MHz): δ 2.47 (s, 3H), 2.56 (s, 3H), 3.93 (s, 3H), 3.95 (s, 3H), 6.57 (d, 1H, J=4.9 Hz), 7.14 (d, 1H, J=8.3 Hz), 7.38–7.41 (m, 1H), 7.49 (s, 1H), 7.80 (s, 1H), 8.17 (t, 1H, J=9.0 Hz), 8.51 (d, 1H, J=5.4 Hz), 9.17 (s, 1H), 11.23 (br, 1H)

Mass spectrometry value (ESI-MS, m/z): 495 (M$^+$−1)

Example 37

N-(5-Chloro-1,3-thiazol-2-yl)-N'-{4-[(6,7-dimethoxy-4-guinolyl)oxy]-2-fluorophenyl}urea 4-[(6,7-Dimethoxy-4-quinolyl)oxy]-2-fluoroaniline (30 mg) was dissolved in chloroform (3 ml) to prepare a solution. Triethylamine (0.3 ml) and a solution of triphosgene (27 mg) in chloroform (0.2 ml) were then added to the solution, and the mixture was stirred at room temperature for 30 min. Next, a solution of 2-amino-5-chlorothiazole (70 mg) in chloroform (0.6 ml) was added thereto, and the mixture was further stirred at room temperature overnight. Water was added to the reaction solution, and the mixture was subjected to separatory extraction with chloroform. The extract was washed with saturated brine and was dried over anhydrous sodium sulfate. The organic layer was concentrated under the reduced pressure, and the residue was purified by chromatography on silica gel using chloroform/ acetone for development to give 12 mg of the title compound.

$^1$H-NMR (CDCl$_3$, 400 MHz): δ 3.94 (s, 3H), 3.95 (s, 3H), 6.57 (d, 1H, J=5.4 Hz), 7.13–7.15 (m, 1H), 7.37–7.40 (m,

1H), 7.41 (s, 1H), 7.44 (s, 1H), 7.49 (s, 1H), 8.16 (t, 1H, J=9.0 Hz), 8.51 (d, 1H, J=5.1 Hz), 9.00 (s, 1H), 11.01 (br, 1H)

Mass spectrometry value (ESI-MS, m/z): 473 ($M^+$−1)

Example 38

N-{2-Chloro-4-[(6,7-dimethoxy-4-quinazolinyl)oxy]phenyl}-N'-(1,3-thiazol-2-yl)urea 2-Chloro-4-[(6,7-dimethoxy-4-quinazolinyl)oxy]-aniline (100 mg) was dissolved in chloroform (5 ml) and triethylamine (0.5 ml) to prepare a solution. A solution of triphosgene (100 mg) in chloroform was then added to the solution, and the mixture was stirred at room temperature for 15 min. Next, 2-aminothiazole (49 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 31 mg of the title compound.

$^1$H-NMR (CDCl$_3$, 400 MHz): δ 8.61 (1H, s), 8.47 (1H, d, J=9.0 Hz), 7.51 (1H, s), 7.44 (1H, d, J=3.6 Hz), 7.36 (1H, d, J=2.7 Hz), 7.31 (1H, s), 7.18–7.24 (1H, m), 6.91 (1H, d, J=3.7 Hz), 4.05 (3H, s), 4.05 (3H, s)

Mass spectrometry value (ESI-MS, m/z): 456 ($M^+$−1)

Example 39

N-{2-Chloro-4-[(6,7-dimethoxy-4-quinazolinyl)oxy]phenyl}-N'-(5-methyl-1,3-thiazol-2-yl)urea 2-Chloro-4-[(6,7-dimethoxy-4-quinazolinyl)oxy]-aniline (100 mg) was dissolved in chloroform (5 ml) and triethylamine (0.5 ml) to prepare a solution. A solution of triphosgene (100 mg) in chloroform was then added to the solution, and the mixture was stirred at room temperature for 15 min. Next, 2-amino-5-methylthiazole (58 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 18 mg of the title compound.

$^1$H-NMR (CDCl$_3$, 400 MHz): δ 8.56 (1H, s), 8.41 (1H, d, J=9.0 Hz), 7.45 (1H, s), 7.29 (1H, d, J=2.7 Hz), 7.26 (1H, s), 7.13 (1H, dd, J=2.7 Hz, J=9.0 Hz), 7.00 (1H, d, J=1.4 Hz), 4.00 (3H, s), 3.99 (3H, s), 2.34 (3H, d, J=1.0 Hz)

Mass spectrometry value (ESI-MS, m/z): 470 ($M^+$−1)

Example 40

N-{2-Chloro-4-[(6,7-dimethoxy-4-quinazolinyl)oxy]phenyl}-N'-(4,5-dimethyl-1,3-thiazol-2-yl)urea 2-Chloro-4-[(6,7-dimethoxy-4-quinazolinyl)oxy]-aniline (100 mg) was dissolved in chloroform (5 ml) and triethylamine (0.5 ml) to prepare a solution. A solution of triphosgene (100 mg) in chloroform was then added to the solution, and the mixture was stirred at room temperature for 15 min. Next, 2-amino-4,5-dimethylthiazole hydrochloride (50 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 33 mg of the title compound.

$^1$H-NMR (CDCl$_3$, 400 MHz): δ 8.61 (1H, s), 8.48 (1H, d, J=9.0 Hz), 7.51 (1H, s), 7.34 (1H, d, J=2.7 Hz), 7.31 (1H, s), 7.17 (1H, dd, J=2.7 Hz, J=9.0 Hz), 4.05 (3H, s), 4.05 (3H, s), 2.26 (3H, s), 2.24 (3H, s)

Mass spectrometry value (ESI-MS, m/z): 484 ($M^+$−1)

Example 41

N-{2-Chloro-4-[(6,7-dimethoxy-4-quinazolinyl)oxy]phenyl}-N'-(4-methyl-1,3-thiazol-2-yl)urea 2-Chloro-4-[(6,7-dimethoxy-4-quinazolinyl)oxy]-aniline (100 mg) was dissolved in chloroform (5 ml) and triethylamine (0.5 ml) to prepare a solution. A solution of triphosgene (100 mg) in chloroform was then added to the solution, and the mixture was stirred at room temperature for 15 min. Next, 2-amino-4-methylthiazole (60 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 15 mg of the title compound.

$^1$H-NMR (CDCl$_3$, 400 MHz): δ 8.57 (1H, d, J=3.0 Hz), 8.43 (1H, d, J=9.0 Hz), 7.46 (1H, s), 7.30–7.35 (1H, m), 7.24–7.28 (1H, m), 7.10–7.20 (1H, m), 6.35 (1H, s), 4.00 (6H, s), 2.31 (3H, d, J=1.0 Hz)

Mass spectrometry value (ESI-MS, m/z): 470 ($M^+$−1)

Example 42

N-{4-[(6,7-Dimethoxy-4-quinazolinyl)oxy]-phenyl}-N'-(1,3-thiazol-2-yl)urea

4-[(6,7-Dimethoxy-4-quinazolinyl)oxy]aniline (40 mg) was dissolved in chloroform (1.2 ml) and triethylamine (0.1 ml) to prepare a solution. A solution of triphosgene (20 mg) in chloroform was then added to the solution, and the mixture was stirred at room temperature for 5 min. Next, 2-aminothiazole (15 mg) was added thereto, and the mixture was further stirred at room temperature overnight. Water was added to the reaction solution, and the mixture was subjected to separatory extraction with chloroform. The organic layer was concentrated, and the residue was then purified by chromatography (chloroform:acetone=2:1) to give the title compound (19.0 mg, yield 33.4%).

$^1$H-NMR (DMSO-d$_6$, 400 MHz): δ 3.99 (d, J=4.88 Hz, 6H), 7.12 (br, 1H), 7.26 (d, J=8.78 Hz, 2H), 7.37–7.39 (m, 2H), 7.55–7.59 (m, 3H), 8.54 (s, 1H)

Mass spectrometry value (ESI-MS, m/z): 422 ($M^+$−1)

Example 43

N-{4-[(6,7-Dimethoxy-4-quinazolinyl)oxy]-phenyl}-N'-(5-methyl-1,3-thiazol-2-yl)urea 4-[(6,7-Dimethoxy-4-quinazolinyl)oxy]aniline (40 mg) was dissolved in chloroform (1.2 ml) and triethylamine (0.1 ml) to prepare a solution. A solution of triphosgene (20 mg) in chloroform was then added to the solution, and the mixture was stirred at room temperature for 5 min. Next, 2-amino-5-methylthiazole (17 mg) was added thereto, and the mixture was further stirred at room temperature overnight. Water was added to the reaction solution, and the mixture was subjected to separatory extraction with chloroform. The organic layer was concentrated, and the residue was then purified by chromatography (chloroform:acetone=2:1) to give the title compound (22.5 mg, yield 38.2%).

$^1$H-NMR (CDCl$_3$, 400 MHz): δ 2.38 (d, J=1.2 Hz, 3H), 4.07 (s, 6H), 6.96 (d, J=1.5 Hz, 1H), 7.21 (dd, J=2.2 Hz, 9.0

Hz, 2H), 7.32 (s, 1H), 7.56 (s, 1H), 7.61 (dd, J=2.20, 9.03 Hz, 2H), 8.60 (s, 1H)

Mass spectrometry value (ESI-MS, m/z): 436 (M$^+$−1)

Example 44
N-{4-[(6,7-Dimethoxy-4-quinazolinyl)oxy]-phenyl}-N'-(4-methyl-1,3-thiazol-2-yl)urea 4-[(6,7-Dimethoxy-4-quinazolinyl)oxy]aniline (40 mg) was dissolved in chloroform (1.2 ml) and triethylamine (0.1 ml) to prepare a solution. A solution of triphosgene (20 mg) in chloroform was then added to the solution, and the mixture was stirred at room temperature for 5 min. Next, 2-amino-4-methylthiazole (17 mg) was added thereto, and the mixture was further stirred at room temperature overnight. Water was added to the reaction solution, and the mixture was subjected to separatory extraction with chloroform. The organic layer was concentrated, and the residue was then purified by chromatography (chloroform:acetone=2:1) to give the title compound (11.8 mg, yield 20.0%).

$^1$H-NMR (CDCl$_3$, 400 MHz): δ 2.38 (d, J=0.97 Hz, 3H), 4.07 (d, J=1.2 Hz, 6H), 6.41 (d, J=1.0 Hz, 1H), 7.23–7.27 (m, 2H), 7.32 (s, 1H), 7.56 (s, 1H), 7.64 (d, J=8.8 Hz, 2H), 8.62 (s, 1H)

Mass spectrometry value (ESI-MS, m/z): 436 (M$^+$−1)

Example 45
N-{4-[(6,7-Dimethoxy-4-quinazolinyl)oxy]-phenyl}-N'-(4,5-dimethyl-1,3-thiazol-2-yl)urea 4-[(6,7-Dimethoxy-4-quinazolinyl)oxy]aniline (40 mg) was dissolved in chloroform (1.2 ml) and triethylamine (0.2 ml) to prepare a solution. A solution of triphosgene (20 mg) in chloroform was then added to the solution, and the mixture was stirred at room temperature for 5 min. Next, 2-amino-4,5-dimethylthiazole hydrochloride (24 mg) was added thereto, and the mixture was further stirred at room temperature overnight. Water was added to the reaction solution, and the mixture was subjected to separatory extraction with chloroform. The organic layer was concentrated, and the residue was then purified by chromatography (chloroform:acetone=2:1) to give the title compound (25.8 mg, yield 42%).

$^1$H-NMR (DMSO-d$_6$, 400 MHz): δ 2.12 (s, 3H), 2.21 (s, 3H), 3.98 (d, J=5.1 Hz, 6H), 7.24 (d, J=8.8 Hz, 2H), 7.38 (s, 1H), 7.56 (s, 1H), 7.57 (d, J=7.3 Hz, 2H), 8.54 (s, 1H)

Mass spectrometry value (ESI-MS, m/z): 450 (M$^+$−1)

Example 46
N-{3-Chloro-4-[(6,7-dimethoxy-4-quinazolinyl)oxy]phenyl}-N'-(1,3-thiazol-2-yl)urea 3-Chloro-4-[(6,7-dimethoxy-4-quinazolinyl)oxy]-aniline (84 mg) was dissolved in chloroform (2.5 ml) and triethylamine (0.25 ml) to prepare a solution. A solution of triphosgene (38 mg) in chloroform was then added to the solution, and the mixture was stirred at room temperature for 5 min. Next, 2-aminothiazole (28 mg) was added thereto, and the mixture was further stirred at room temperature overnight. Water was added to the reaction solution, and the mixture was subjected to separatory extraction with chloroform. The organic layer was concentrated and was evaporated to dryness. Next, diethyl ether was added to the solid, and the solid was then collected by filtration. Further, the collected solid was washed with methyl alcohol to give the title compound (77.5 mg, yield 66%).

$^1$H-NMR (DMSO-d$_6$, 400 MHz): δ 3.99 (d, J=5.4 Hz, 6H), 7.13 (br, 1H), 7.38 (d, J=3.7 Hz, 1H), 7.41 (s, 1H), 7.43 (s, 1H), 7.46 (dd, J=2.2 Hz, 8.8 Hz, 1H), 7.58 (s, 1H), 7.89 (d, J=1.7 Hz, 1H), 8.54 (s, 1H)

Mass spectrometry value (ESI-MS, m/z): 456 (M$^+$−1)

Example 47
N-{3-Chloro-4-[(6,7-dimethoxy-4-quinazolinyl)oxy]phenyl}-N'-(5-methyl-1,3-thiazol-2-yl)urea 3-Chloro-4-[(6,7-dimethoxy-4-quinazolinyl)oxy]-aniline (84 mg) was dissolved in chloroform (2.5 ml) and triethylamine (0.25 ml) to prepare a solution. A solution of triphosgene (38 mg) in chloroform was then added to the solution, and the mixture was stirred at room temperature for 5 min. Next, 2-amino-5-methylthiazole (32 mg) was added thereto, and the mixture was further stirred at room temperature overnight. Water was added to the reaction solution, and the mixture was subjected to separatory extraction with chloroform. The organic layer was concentrated and was evaporated to dryness. Diethyl ether was then added to the solid, and the solid was collected by filtration. Further, the collected solid was washed with methyl alcohol to give the title compound (81.5 mg, yield 70%).

$^1$H-NMR (DMSO-d$_6$, 400 MHz): δ 2.32 (s, 3H), 3.99 (d, J=5.6 Hz, 6H), 7.04 (br, 1H), 7.40–7.47 (m, 3H), 7.58 (s, 1H), 7.88 (br, 1H), 8.55 (s, 1H)

Mass spectrometry value (ESI-MS, m/z): 470 (M$^+$−1)

Example 48
N-{3-Chloro-4-[(6,7-dimethoxy-4-quinazolinyl)oxy]phenyl}-N'-(4-methyl-1,3-thiazol-2-yl)urea 3-Chloro-4-[(6,7-dimethoxy-4-quinazolinyl)oxy]-aniline (84 mg) was dissolved in chloroform (2.5 ml) and triethylamine (0.25 ml) to prepare a solution. A solution of triphosgene (38 mg) in chloroform was then added to the solution, and the mixture was stirred at room temperature for 5 min. Next, 2-amino-4-methylthiazole (32 mg) was added thereto, and the mixture was further stirred at room temperature overnight. Water was added to the reaction solution, and the mixture was subjected to separatory extraction with chloroform. The organic layer was concentrated and was evaporated to dryness. Next, diethyl ether was added to the solid, and the solid was collected by filtration. Further, the collected solid was washed with methyl alcohol to give the title compound (78.3 mg, yield 68%).

$^1$H-NMR (DMSO-d$_6$, 400 MHz): δ 2.23 (s, 3H), 3.99 (d, J=5.61 Hz, 6H), 6.64 (Br, 1H), 7.39–7.48 (m, 3H), 7.58 (s, 1H), 7.89 (br, 1H), 8.54 (s, 1H)

Mass spectrometry value (ESI-MS, m/z): 470 (M$^+$−1)

Example 49
N-{3-Chloro-4-[(6,7-dimethoxy-4-quinazolinyl)oxy]phenyl}-N'-(4,5-dimethyl-1,3-thiazol-2-yl)urea 3-Chloro-4-[(6,7-dimethoxy-4-quinazolinyl)oxy]-aniline (84 mg) was dissolved in chloroform (2.5 ml) and triethylamine (0.50 ml) to prepare a solution. A solution of triphosgene (38 mg) in chloroform was then added to the solution, and the mixture was stirred at room temperature for 5 min. Next, 2-amino-4,5-dimethylthiazole hydrochloride (42 mg) was added thereto, and the mixture was further stirred at room temperature overnight. Water was added to the reaction solution, and the mixture was subjected to separatory extraction with chloroform. The organic layer was concentrated and was evaporated to dryness. Diethyl ether was then added to the solid, and the solid was collected by filtration. Further, the collected solid was washed with methyl alcohol to give the title compound (86.4 mg, yield 68%).

$^1$H-NMR (DMSO-d$_6$, 400 MHz): δ 2.13 (s, 3H), 2.20 (s, 3H), 3.99 (d, J=5.9 Hz, 6H), 7.38–7.49 (m, 3H), 7.57 (s, 1H), 7.88 (br, 1H), 8.54 (s, 1H)

Mass spectrometry value (ESI-MS, m/z): 484 (M$^+$−1)

Example 50
N-{4-[(6,7-Dimethoxy-4-quinolyl)oxy]phenyl}-N'-[5-(trifluoromethyl)-1,3,4-thiadiazol-2-yl]urea 4-[(6,7-Dimethoxy-4-quinolyl)oxy]aniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-trifluoromethyl-1,3,4-thiadiazole (70 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 43 mg of the title compound.

$^1$H-NMR (CDCl$_3$, 400 MHz): δ 8.45–8.50 (1H, m), 7.53–7.56 (1H, m), 7.48–7.52 (1H, m), 7.39–7.43 (1H, m), 7.00–7.24 (2H, m), 6.42–6.48 (1H, m), 4.03 (6H, s)

Mass spectrometry value (ESI-MS, m/z): 490 (M$^+$−1)

Example 51
N-{4-[(6,7-Dimethoxy-4-quinolyl)oxy]-2-fluorophenyl}-N'-[5-(trifluoromethyl)-1,3,4-thiadiazol-2-yl]urea 4-[(6,7-Dimethoxy-4-quinolyl)oxy]-2-fluoroaniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-trifluoromethyl-1,3,4-thiadiazole (70 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 62 mg of the title compound.

$^1$H-NMR (CDCl$_3$, 400 MHz): δ 8.52 (1H, d, J=5.4 Hz), 8.20 (1H, dd, J=8.9 Hz, J=8.9 Hz), 7.48 (1H, s), 7.44 (1H, s), 7.00–7.08 (2H, m), 6.53 (1H, d, J=5.1 Hz), 4.04 (3H, s), 4.03 (3H, s)

Mass spectrometry value (ESI-MS, m/z): 508 (M$^+$−1)

Example 52
N-{4-[(6,7-Dimethoxy-4-quinolyl)oxy]-3-fluorophenyl}-N'-[5-(trifluoromethyl)-1,3,4-thiadiazol-2-yl]urea 4-[(6,7-Dimethoxy-4-quinolyl)oxy]-3-fluoroaniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-trifluoromethyl-1,3,4-thiadiazole (70 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 72 mg of the title compound.

$^1$H-NMR (CDCl$_3$, 400 MHz): δ 8.30–8.60 (1H, m), 7.00–7.70 (5H, m), 6.30–6.50 (1H, m), 4.05 (3H, s), 4.03 (3H, s)

Mass spectrometry value (ESI-MS, m/z): 508 (M$^+$−1)

Example 53
N-{4-[(6,7-Dimethoxy-4-quinolyl)oxy]-2,3-dimethylphenyl}-N'-[5-(trifluoromethyl)-1,3,4-thiadiazol-2-yl]urea 4-[(6,7-Dimethoxy-4-quinolyl)oxy]-2,3-dimethylaniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-trifluoromethyl-1,3,4-thiadiazole (68 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 70 mg of the title compound.

$^1$H-NMR (CDCl$_3$, 400 MHz): δ 8.40 (1H, d, J=6.6 Hz), 7.60–7.65 (1H, m), 7.55 (1H, s), 7.39 (1H, s), 6.99 (1H, d, J=8.8 Hz), 6.24 (1H, d, J=5.4 Hz), 4.01 (3H, s), 3.99 (3H, s), 2.30 (3H, s), 2.12 (3H, s)

Mass spectrometry value (ESI-MS, m/z): 518 (M$^+$−1)

Example 54
N-{4-[(6,7-Dimethoxy-4-quinolyl)oxy]phenyl}-N'-(5-methyl-1,3,4-thiadiazol-2-yl)urea 4-[(6,7-Dimethoxy-4-quinolyl)oxy]aniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-methyl-1,3,4-thiadiazole (47 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 49 mg of the title compound.

$^1$H-NMR (CDCl$_3$, 400 MHz): δ 8.41 (1H, d, J=5.4 Hz), 7.56 (2H, d, J=8.6 Hz), 7.50 (1H, s), 7.35 (1H, s), 7.20–7.25 (2H, m), 7.07 (2H, d, J=9.0 Hz), 6.38 (1H, d, J=5.1 Hz), 3.98 (6H, s), 2.46 (3H, s)

Mass spectrometry value (ESI-MS, m/z): 436 (M$^+$−1)

Example 55
N-{4-[(6,7-Dimethoxy-4-quinolyl)oxy]-2-methylphenyl}-N'-(5-methyl-1,3,4-thiadiazol-2-yl)urea 4-[(6,7-Dimethoxy-4-quinolyl)oxy]-2-methylaniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-methyl-1,3,4-thiadiazole (49 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 40 mg of the title compound.

$^1$H-NMR (CDCl$_3$, 400 MHz): δ 8.46 (1H, d, J=5.4 Hz), 8.03–8.15 (1H, m), 7.54 (1H, s), 7.40 (1H, s), 6.95–7.07 (3H, m), 6.46 (1H, d, J=5.2 Hz), 4.03 (6H, s), 2.51 (3H, s), 2.28 (3H, s)

Mass spectrometry value (ESI-MS, m/z): 450 (M$^+$−1)

Example 56

N-{4-[(6,7-Dimethoxy-4-guinolyl)oxy]-3-methylphenyl}-N'-(5-methyl-1,3,4-thiadiazol-2-yl)urea 4-[(6,7-Dimethoxy-4-quinolyl)oxy]-3-methylaniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-methyl-1,3,4-thiadiazole (49 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 58 mg of the title compound.

$^1$H-NMR (CDCl$_3$, 400 MHz): δ 8.38 (1H, d, J=5.4 Hz), 7.53 (1H, s), 7.48 (1H, s), 7.36 (1H, s), 7.15–7.21 (2H, m), 6.25 (1H, d, J=5.4 Hz), 4.00 (3H, s), 3.99 (3H, s), 2.43 (3H, s), 2.06 (3H, s)

Mass spectrometry value (ESI-MS, m/z): 450 (M$^+$–1)

Example 57

N-{4-[(6,7-Dimethoxy-4-guinolyl)oxy]-2,3-dimethylphenyl}-N'-(5-methyl-1,3,4-thiadiazol-2-yl)urea 4-[(6,7-Dimethoxy-4-quinolyl)oxy]-2,3-dimethylaniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-methyl-1,3,4-thiadiazole (43 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 52 mg of the title compound.

$^1$H-NMR (CDCl$_3$, 400 MHz): δ 8.36 (1H, d, J=8.5 Hz), 7.71 (1H, d), 7.55 (1H, s), 7.36 (1H, s), 7.90–7.00 (2H, m), 6.21 (1H, d, J=5.1 Hz), 4.00 (3H, s), 3.98 (3H, s), 2.45 (3H, s), 2.18 (3H, s), 2.05 (3H, s)

Mass spectrometry value (ESI-MS, m/z): 464 (M$^+$–1)

Example 58

N-{4-[(6,7-Dimethoxy-4-quinolyl)oxy]-2-fluorophenyl}-N'-(5-methyl-1,3,4-thiadiazol-2-yl)urea 4-[(6,7-Dimethoxy-4-quinolyl)oxy]-2-fluoroaniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-methyl-1,3,4-thiadiazole (52 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 52 mg of the title compound.

$^1$H-NMR (CDCl$_3$, 400 MHz): δ 8.46 (1H, d, J=5.4 Hz), 8.20–8.30 (1H, m), 7.44–7.46 (1H, m), 7.37 (1H, s), 6.90–7.00 (2H, m), 6.47 (1H, d, J=5.4 Hz), 3.99 (3H, s), 3.98 (3H, s), 2.64 (3H, s)

Mass spectrometry value (ESI-MS, m/z): 454 (M$^+$–1)

Example 59

N-{4-[(6,7-Dimethoxy-4-guinolyl)oxy]phenyl}-N'-(5-ethyl-1,3,4-thiadiazol-2-yl)urea 4-[(6,7-Dimethoxy-4-quinolyl)oxy]aniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-ethyl-1,3,4-thiadiazole (45 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 72 mg of the title compound.

$^1$H-NMR (CDCl$_3$, 400 MHZ): δ 8.43 (1H, d, J=5.4 Hz), 7.63 (2H, d, J=8.8 Hz), 7.51 (1H, s), 7.37 (1H, s), 7.11 (2H, d, J=9.0 Hz), 6.41 (1H, d, J=5.1 Hz), 3.99 (3H, s), 3.99 (3H, s), 3.03 (2H, q, J=7.6 Hz), 1.41 (3H, t, J=7.6 Hz)

Mass spectrometry value (ESI-MS, m/z): 450 (M$^+$–1)

Example 60

N-{4-[(6,7-Dimethoxy-4-guinolyl)oxy]-2-methylphenyl}-N'-(5-ethyl-1,3,4-thiadiazol-2-yl)urea 4-[(6,7-Dimethoxy-4-quinolyl)oxy]-2-methylaniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-ethyl-1,3,4-thiadiazole (42 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 68 mg of the title compound.

$^1$H-NMR (CDCl$_3$, 400 MHz): δ 8.43 (1H, d, J=5.4 Hz), 7.90 (1H, d, J=8.0 Hz), 7.49 (1H, s), 7.37 (1H, s), 6.98–7.05 (2H, m), 6.44 (1H, d, J=5.4 Hz), 3.99 (6H, s), 2.98 (2H, q, J=7.6 Hz), 2.39 (3H, s), 1.36 (3H, t, J=7.6 Hz)

Mass spectrometry value (ESI-MS, m/z): 464 (M$^+$–1)

Example 61

N-{4-[(6,7-Dimethoxy-4-guinolyl)oxy]-3-methylphenyl}-N'-(5-ethyl-1,3,4-thiadiazol-2-yl)urea 4-[(6,7-Dimethoxy-4-quinolyl)oxy]-3-methylaniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-ethyl-1,3,4-thiadiazole (43 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 71 mg of the title compound.

$^1$H-NMR (CDCl$_3$, 400 MHz): δ 8.39 (1H, d, J=5.4 Hz), 8.17 (1H, s), 7.53 (1H, s), 7.48 (1H, d, J=2.2 Hz), 7.36 (1H, s), 7.18–7.30 (2H, m), 6.28 (1H, d, J=5.2 Hz), 4.00 (3H, s), 3.99 (3H, s), 2.90 (2H, q, J=7.6 Hz), 2.09 (3H, s), 1.27 (3H, t, J=7.6 Hz)

Mass spectrometry value (ESI-MS, m/z): 464 (M$^+$−1)

Example 62
N-{4-[(6,7-Dimethoxy-4-guinolyl)oxy]-2,3-dimethylphenyl}-N'-(5-ethyl-1,3,4-thiadiazol-2-yl)urea 4-[(6,7-Dimethoxy-4-quinolyl)oxy]-2,3-dimethylaniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-ethyl-1,3,4-thiadiazole (44 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 53 mg of the title compound.

$^1$H-NMR (CDCl$_3$, 400 MHz): δ 8.38 (1H, d, J=5.1 Hz), 7.64 (1H, d, J=8.5 Hz), 7.56 (1H, s), 7.37 (1H, s), 6.97 (1H, d, J=8.8 Hz), 6.24 (1H, d, J=5.1 Hz), 4.01 (3H, s), 3.99 (3H, s), 2.99 (2H, q, J=7.6 Hz), 2.32 (3H, s), 2.10 (3H, s), 1.36 (3H, t, J=7.6 Hz)

Mass spectrometry value (ESI-MS, m/z): 478, 479 (M$^+$−1)

Example 63
N-{4-[(6,7-Dimethoxy-4-guinolyl)oxy]-2-fluorophenyl}-N'-(5-ethyl-1,3,4-thiadiazol-2-yl)urea 4-[(6,7-Dimethoxy-4-quinolyl)oxy]-2-fluoroaniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-ethyl-1,3,4-thiadiazole (43 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 49 mg of the title compound.

$^1$H-NMR (CDCl$_3$, 400 MHz): δ 8.46 (1H, d, J=5.4 Hz), 8.22 (1H, q, J=9.1 Hz), 7.45 (1H, s), 7.37 (1H, s), 6.92–7.00 (2H, m), 6.47 (1H, d, J=5.4 Hz), 3.99 (3H, S), 3.98 (3H, S), 3.01 (2H, q, J=7.6 Hz), 1.38 (3H, t, J=7.6 Hz)

Mass spectrometry value (ESI-MS, m/z): 468, 469 (M$^+$−1)

Example 64
N-{4-[(6,7-Dimethoxy-4-guinolyl)oxy]-3-fluorophenyl}-N'-(5-ethyl-1,3,4-thiadiazol-2-yl)urea 4-[(6,7-Dimethoxy-4-quinolyl)oxy]-3-fluoroaniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-ethyl-1,3,4-thiadiazole (41 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 53 mg of the title compound.

$^1$H-NMR (CDCl$_3$, 400 MHz): δ 8.44 (1H, d, J=5.1 Hz), 8.26 (1H, bs), 7.68 (1H, dd, J=2.4 Hz, J=12.0 Hz), 7.53 (1H, s), 7.37 (1H, s), 7.28–7.33 (1H, m), 7.15–7.22 (2H, m), 6.37 (1H, dd, J=1.0 Hz, J=5.4 Hz), 4.00 (3H, s), 3.99 (3H, s), 3.04 (2H, q, J=7.5 Hz), 1.41 (3H, t, J=7.6 Hz)

Mass spectrometry value (ESI-MS, m/z): 468 (M$^+$−1)

Example 65
N-{2-Chloro-4-[(6,7-dimethoxy-4-guinolyl)oxy]phenyl}-N'-(5-ethyl-1,3,4-thiadiazol-2-yl)urea 2-Chloro-4-[(6,7-dimethoxy-4-quinolyl)oxy]aniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-ethyl-1,3,4-thiadiazole (41 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 21 mg of the title compound.

$^1$H-NMR (CDCl$_3$, 400 MHz): δ 8.46 (1H, d, J=5.2 Hz), 8.25 (1H, d, J=9.0 Hz), 7.45 (1H, s), 7.37 (1H, s), 7.22 (1H, d, J=2.7 Hz), 7.09 (1H, dd, J=2.7 Hz, J=9.0 Hz), 6.46 (1H, d, J=5.2 Hz), 3.99 (3H, s), 3.98 (3H, s), 2.99 (2H, q, J=7.6 Hz), 1.37 (3H, t, J=7.6 Hz)

Mass spectrometry value (ESI-MS, m/z): 484 (M$^+$−1)

Example 66
N-{3-Chloro-4-[(6,7-dimethoxy-4-guinolyl)oxy]phenyl}-N'-(5-ethyl-1,3,4-thiadiazol-2-yl)urea 3-Chloro-4-[(6,7-dimethoxy-4-quinolyl)oxy]aniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-ethyl-1,3,4-thiadiazole (41 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 48 mg of the title compound.

$^1$H-NMR (CDCl$_3$, 400 MHz): δ 8.48 (1H, d, J=5.4 Hz), 7.92 (1H, d, J=2.7 Hz), 7.59 (1H, s), 7.45–7.52 (2H, m), 7.17 (1H, d, J=8.8 Hz), 6.33 (1H, d, J=5.4 Hz), 4.05 (3H, s), 4.04 (3H, s), 3.01 (2H, q, J=7.6 Hz), 1.40 (3H, t, J=7.6 Hz)

Mass spectrometry value (ESI-MS, m/z): 484, 486 (M$^+$−1)

Example 67
N-{2-Chloro-4-[(6,7-dimethoxy-4-quinolyl)oxy]phenyl}-N'-(5-cyclopropyl-1,3,4-thiadiazol-2-yl)urea 2-Chloro-4-[(6,7-dimethoxy-4-quinolyl)oxy]aniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-cyclopropyl-1,3,4-thiadiazole (55 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 32 mg of the title compound.

$^1$H-NMR (CDCl$_3$, 400 MHz): δ 8.51 (1H, d, J=5.4 Hz), 8.29 (1H, d, J=9.0 Hz), 7.50 (1H, s), 7.42 (1H, s), 7.27 (1H, d, J=2.7 Hz), 7.14 (1H, d, d, J=2.7 Hz, J=9.0 Hz), 6.51 (1H, d, J=5.1 Hz), 4.04 (3H, s), 4.03 (3H, s), 2.23–2.31 (1H, m), 1.07–1.23 (4H, m)

Mass spectrometry value (ESI-MS, m/z): 496, 498 (M$^+$−1)

Example 68
N-{3-Chloro-4-[(6,7-dimethoxy-4-quinolyl)oxy]phenyl}-N'-(5-cyclopropyl-1,3,4-thiadiazol-2-yl)urea 3-Chloro-4-[(6,7-dimethoxy-4-quinolyl)oxy]aniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-cyclopropyl-1,3,4-thiadiazole (55 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 42 mg of the title compound.

$^1$H-NMR (CDCl$_3$, 400 MHz): δ 8.43 (1H, d, J=5.4 Hz), 8.37 (1H, brs), 7.81 (1H, d, J=2.4 Hz), 7.54 (1H, s), 7.50 (1H, dd, J=8.8 Hz, J=2.7 Hz), 7.37 (1H, s), 7.16 (1H, d, J=8.8 Hz), 6.28 (1H, d, J=5.4 Hz), 4.01 (3H, s), 3.99 (3H, s), 2.22–2.31 (1H, m), 1.15–1.22 (2H, m), 1.12–1.08 (2H, m)

Mass spectrometry value (ESI-MS, m/z): 496 (M$^+$−1)

Example 69
N-(5-Cyclopropyl-1,3,4-thiadiazol-2-yl)-N'-{4-[(6,7-dimethoxy-4-quinolyl)oxy]-2,5-dimethylphenyl}-urea 4-[(6,7-Dimethoxy-4-quinolyl)oxy]-2,5-dimethylaniline (100 mg) was dissolved in chloroform (5 ml) and diisopropylethylamine (0.5 ml) to prepare a solution. A solution of triphosgene (100 mg) in chloroform was then added to the solution, and the mixture was stirred at room temperature for 15 min. Next, 2-amino-5-cyclopropyl-1,3,4-thiadiazole (55 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 55 mg of the title compound.

$^1$H-NMR (CDCl$_3$, 400 MHz): 8.40 (1H, d, J=5.4 Hz), 7.80 (1H, s), 7.54 (1H, s), 7.37 (1H, s), 6.91 (1H, s), 6.27 (1H, d, J=5.4 Hz), 5.27 (1H, brs), 4.00 (3H, s), 3.99 (3H, s), 2.34 (3H, s), 2.13–2.27 (1H, m), 2.11 (3H, s), 1.10–1.20 (2H, m), 0.98–1.08 (2H, m)

Mass spectrometry value (ESI-MS, m/z): 490 (M$^+$−1)

Example 70
N-{4-[(6,7-Dimethoxy-4-quinolyl)oxy]-2-fluorophenyl}-N'-[5-(ethylsulfanyl)-1,3,4-thiadiazol-2-yl]urea 4-[(6,7-Dimethoxy-4-quinolyl)oxy]-2-fluoroaniline (100 mg) was dissolved in chloroform (5 ml) and triethylamine (0.5 ml) to prepare a solution. A solution of triphosgene (100 mg) in chloroform was then added to the solution, and the mixture was stirred at room temperature for 15 min. Next, 2-amino-5-ethylthio-1,3,4-thiadiazole (55 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 31 mg of the title compound.

$^1$H-NMR (CDCl$_3$, 400 MHz): δ 8.45 (1H, d, J=5.1 Hz), 8.18 (1H, dd, J=9.1 Hz, J=9.1 Hz), 8.09 (1H, brs), 7.44 (1H, s), 7.37 (1H, s), 6.90–7.00 (2H, m), 6.47 (1H, d, J=5.2 Hz), 3.99 (3H, s), 3.98 (3H, s), 3.16 (2H, q, J=7.3 Hz), 1.37 (3H, t, J=7.3 Hz)

Mass spectrometry value (ESI-MS, m/z): 500 (M$^+$−1)

Example 71
N-{4-[(6,7-Dimethoxy-4-quinolyl)oxy]-2,3-dimethylphenyl}-N'-[5-(ethylsulfanyl)-1,3,4-thiadiazol-2-yl]urea 4-[(6,7-Dimethoxy-4-quinolyl)oxy]-2,3-dimethylaniline (100 mg) was dissolved in chloroform (5 ml) and triethylamine (0.5 ml) to prepare a solution. A solution of triphosgene (100 mg) in chloroform was then added to the solution, and the mixture was stirred at room temperature for 15 min. Next, 2-amino-5-ethylthio-1,3,4-thiadiazole (60 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 53 mg of the title compound.

$^1$H-NMR (CDCl$_3$, 400 MHz): δ 8.38 (1H, d, J=5.4 Hz), 7.56 (1H, s), 7.52 (1H, d, J=8.8 Hz), 7.37 (1H, s), 6.95 (1H, d, J=8.6 Hz), 6.23 (1H, d, J=5.4 Hz), 4.01 (3H, s), 3.99 (3H, s), 3.13 (2H, q, J=7.3 Hz), 2.28 (3H, s), 2.08 (3H, s), 1.37 (3H, t, J=7.3 Hz)

Mass spectrometry value (ESI-MS, m/z): 510 (M$^+$−1)

Example 72
N-{2-Chloro-4-[(6,7-dimethoxy-4-quinolyl)oxy]phenyl}-N'-[5-(trifluoromethyl)-1,3,4-thiadiazol-2-yl]urea 2-Chloro-4-[(6,7-dimethoxy-4-quinolyl)oxy]aniline (100 mg) was dissolved in chloroform (5 ml) and triethylamine (0.5 ml) to prepare a solution. A solution of triphosgene (100 mg) in chloroform was then added to the solution, and the mixture was stirred at room temperature for 15 min. Next, 2-amino-5-trifluoromethyl-1,3,4-thiadiazole (65 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 48 mg of the title compound.

$^1$H-NMR (CDCl$_3$, 400 MHz): 8.52 (1H, d, J=5.2 Hz), 8.28 (1H, d, J=9.0 Hz), 7.93 (1H, s), 7.48–7.54 (1H, m), 7.38–7.44 (1H, m), 7.29 (1H, d, J=2.7 Hz), 7.10–7.20 (1H, m), 6.52 (1H, d, J=5.2 Hz), 4.04 (3H, s), 4.03 (3H, s)

Mass spectrometry value (ESI-MS, m/z): 524 (M$^+$−1)

Example 73
N-{3-Chloro-4-[(6,7-dimethoxy-4-guinolyl)oxy]phenyl}-N'-[5-(trifluoromethyl)-1,3,4-thiadiazol-2-yl]urea

3-Chloro-4-[(6,7-dimethoxy-4-quinolyl)oxy]aniline (100 mg) was dissolved in chloroform (5 ml) and triethylamine (0.5 ml) to prepare a solution. A solution of triphosgene (100 mg) in chloroform was then added to the solution, and the mixture was stirred at room temperature for 15 min. Next, 2-amino-5-trifluoromethyl-1,3,4-thiadiazole (65 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 63 mg of the title compound 30.

$^1$H-NMR (CDCl$_3$, 400 MHz): δ 8.42 (1H, d, J=5.4 Hz), 7.84 (1H, brs), 7.67 (1H, d, J=2.7 Hz), 7.55 (1H, s), 7.36 (1H, s), 7.30 (1H, dd, J=2.7 Hz, J=8.8 Hz), 7.12 (1H, d, J=8.8 Hz), 6.28 (1H, d, J=5.4 Hz), 4.00 (3H, s), 3.97 (3H, s)

Mass spectrometry value (ESI-MS, m/z): 524 (M$^+$−1)

Example 74
N-[5-(Tert-butyl)-1,3,4-thiadiazol-2-yl]-N'-{4-[(6,7-dimethoxy-4-guinolyl)oxy]-2-fluorophenyl}urea

4-[(6,7-Dimethoxy-4-quinolyl)oxy]-2-fluoroaniline (100 mg) was dissolved in chloroform (5 ml) and triethylamine (0.5 ml) to prepare a solution. A solution of triphosgene (100 mg) in chloroform was then added to the solution, and the mixture was stirred at room temperature for 15 min. Next, 2-amino-5-tert-butyl-1,3,4-thiadiazole (65 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 49 mg of the title compound.

$^1$H-NMR (CDCl$_3$, 400 MHz): δ 8.51 (1H, d, J=5.4 Hz), 8.30 (1H, dd, J=8.9 Hz, J=8.9 Hz), 7.50 (1H, s), 7.42 (1H, s), 6.97–7.04 (2H, m), 6.53 (1H, d, J=5.1 Hz), 4.04 (3H, s), 4.03 (3H, s), 1.39 (9H, s)

Mass spectrometry value (ESI-MS, m/z): 496 (M$^+$−1)

Example 75
N-[5-(Tert-butyl)-1,3,4-thiadiazol-2-yl]-N'-{4-[(6,7-dimethoxy-4-quinolyl)oxy]-2,3-dimethylphenyl}-urea

4-[(6,7-Dimethoxy-4-quinolyl)oxy]-2,3-dimethylaniline (100 mg) was dissolved in chloroform (5 ml) and triethylamine (0.5 ml) to prepare a solution. A solution of triphosgene (100 mg) in chloroform was then added to the solution, and the mixture was stirred at room temperature for 15 min. Next, 2-amino-5-tert-butyl-1,3,4-thiadiazole (65 mg) was added thereto, and the mixture was further stirred at room temperature overnight. Distilled water was added to the reaction solution, and the mixture was subjected to separatory extraction with chloroform. The organic layer was washed with saturated brine and was dried over sodium sulfate. The organic layer was concentrated under the reduced pressure, and the residue was purified by HPLC using chloroform/acetone for development to give 28 mg of the title compound.

$^1$H-NMR (CDCl$_3$, 400 MHz): δ 8.43 (1H, d, J=5.2 Hz), 7.66 (1H, d, J=8.5 Hz), 7.61 (1H, s), 7.42 (1H, s), 7.01 (1H, d, J=8.8 Hz), 6.29 (1H, d, J=5.1 Hz), 4.05 (3H, s), 4.04 (3H, s), 2.37 (3H, s), 2.14 (3H, s), 1.38 (9H, s)

Mass spectrometry value (ESI-MS, m/z): 506 (M$^+$−1)

The structures of the compounds prepared in Examples 1 to 75 can be shown as follows.

TABLE 1

(Ib)

| Ex. | X  | R$^{17}$ | R$^{18}$ | R$^{19}$ | R$^{21}$ | Q  | R$^{22}$ | R$^{23}$ |
|-----|----|----|----|----|------|----|------|------|
| 1   | CH | Cl | H  | H  | (i)  | O  | H    | H    |
| 2   | CH | Cl | H  | H  | (ii) | O  | CH$_3$ | H    |
| 3   | CH | F  | H  | H  | (i)  | O  | H    | H    |
| 4   | CH | H  | Cl | H  | (i)  | O  | CH$_3$ | H    |
| 5   | CH | H  | Cl | H  | (ii) | O  | CH$_3$ | H    |
| 6   | CH | H  | F  | H  | (ii) | O  | CH$_3$ | H    |
| 7   | CH | F  | H  | H  | (ii) | O  | CH$_3$ | H    |
| 8   | CH | F  | H  | H  | (i)  | O  | CH$_3$ | H    |
| 9   | CH | H  | F  | H  | (i)  | O  | CH$_3$ | H    |
| 10  | N  | H  | H  | H  | (i)  | O  | CH$_3$ | H    |
| 11  | N  | H  | H  | H  | (ii) | O  | CH$_3$ | H    |
| 12  | N  | H  | Cl | H  | (i)  | O  | CH$_3$ | H    |
| 13  | N  | H  | Cl | H  | (ii) | O  | CH$_3$ | H    |
| 14  | N  | Cl | H  | H  | (i)  | O  | CH$_3$ | H    |
| 15  | N  | Cl | H  | H  | (ii) | O  | CH$_3$ | H    |
| 16  | N  | H  | H  | H  | (ii) | S  | CH$_3$ | H    |
| 17  | N  | H  | Cl | H  | (ii) | S  | CH$_3$ | H    |
| 18  | N  | Cl | H  | H  | (ii) | S  | CH$_3$ | H    |
| 19  | CH | Cl | H  | H  | (ii) | NH | H    | H    |
| 20  | CH | H  | F  | H  | (ii) | NH | H    | H    |
| 21  | CH | H  | F  | H  | (iii)| S  | CH$_3$ | H    |
| 22  | CH | H  | Cl | H  | (iii)| S  | H    | CH$_3$ |
| 23  | CH | H  | F  | H  | (iii)| S  | CH$_3$ | CH$_3$ |
| 24  | CH | H  | Cl | H  | (iii)| S  | CH$_3$ | CH$_3$ |
| 25  | CH | Cl | H  | H  | (iii)| S  | CH$_3$ | CH$_3$ |
| 26  | CH | H  | CF$_3$ | H  | (iii)| S  | CH$_3$ | CH$_3$ |
| 27  | CH | H  | F  | H  | (iii)| S  | H    | H    |
| 28  | CH | H  | F  | H  | (iii)| S  | H    | CH$_3$ |
| 29  | CH | H  | F  | H  | (iii)| S  | H    | A    |
| 30  | CH | H  | F  | H  | (iii)| S  | H    | tBu  |
| 31  | CH | H  | Cl | H  | (iii)| S  | H    | A    |
| 32  | CH | H  | Cl | H  | (iii)| S  | Br   | H    |
| 33  | CH | H  | Cl | H  | (iii)| S  | H    | tBu  |
| 34  | CH | H  | Cl | H  | (iii)| S  | Cl   | H    |
| 35  | CH | H  | F  | H  | (iii)| S  | Br   | H    |
| 36  | CH | H  | F  | H  | (iii)| S  | Ac   | CH$_3$ |
| 37  | CH | H  | F  | H  | (iii)| S  | Cl   | H    |

TABLE 1-continued (Ib)

[Chemical structure of quinazoline/quinoline compound with MeO groups, R17, R18, R19, R21 substituents, urea linker, and X in the ring]

| Ex. | X  | R17 | R18 | R19 | R21   | Q | R22  | R23  |
|-----|----|-----|-----|-----|-------|---|------|------|
| 38  | N  | H   | Cl  | H   | (iii) | S | H    | H    |
| 39  | N  | H   | Cl  | H   | (iii) | S | CH3  | H    |
| 40  | N  | H   | Cl  | H   | (iii) | S | CH3  | CH3  |
| 41  | N  | H   | Cl  | H   | (iii) | S | H    | CH3  |
| 42  | N  | H   | H   | H   | (iii) | S | H    | H    |
| 43  | N  | H   | H   | H   | (iii) | S | CH3  | H    |
| 44  | N  | H   | H   | H   | (iii) | S | H    | CH3  |
| 45  | N  | H   | H   | H   | (iii) | S | CH3  | CH3  |
| 46  | N  | Cl  | H   | H   | (iii) | S | H    | H    |
| 47  | N  | Cl  | H   | H   | (iii) | S | CH3  | H    |
| 48  | N  | Cl  | H   | H   | (iii) | S | H    | CH3  |
| 49  | N  | Cl  | H   | H   | (iii) | S | CH3  | CH3  |
| 50  | CH | H   | H   | H   | (iv)  | S | CF3  | H    |
| 51  | CH | H   | F   | H   | (iv)  | S | CF3  | H    |
| 52  | CH | F   | H   | H   | (iv)  | S | CF3  | H    |
| 53  | CH | CH3 | CH3 | H   | (iv)  | S | CF3  | H    |
| 54  | CH | H   | H   | H   | (iv)  | S | CH3  | H    |
| 55  | CH | H   | CH3 | H   | (iv)  | S | CH3  | H    |
| 56  | CH | CH3 | H   | H   | (iv)  | S | CH3  | H    |
| 57  | CH | CH3 | CH3 | H   | (iv)  | S | CH3  | H    |
| 58  | CH | H   | F   | H   | (iv)  | S | CH3  | H    |
| 59  | CH | H   | H   | H   | (iv)  | S | Et   | H    |
| 60  | CH | H   | CH3 | H   | (iv)  | S | Et   | H    |
| 61  | CH | CH3 | H   | H   | (iv)  | S | Et   | H    |
| 62  | CH | CH3 | CH3 | H   | (iv)  | S | Et   | H    |
| 63  | CH | H   | F   | H   | (iv)  | S | Et   | H    |
| 64  | CH | F   | H   | H   | (iv)  | S | Et   | H    |
| 65  | CH | H   | Cl  | H   | (iv)  | S | Et   | H    |
| 66  | CH | Cl  | H   | H   | (iv)  | S | Et   | H    |
| 67  | CH | H   | Cl  | H   | (iv)  | S | cPr  | H    |
| 68  | CH | Cl  | H   | H   | (iv)  | S | cPr  | H    |
| 69  | CH | H   | CH3 | CH3 | (iv)  | S | cPr  | H    |
| 70  | CH | H   | F   | H   | (iv)  | S | EtS  | H    |
| 71  | CH | CH3 | CH3 | H   | (iv)  | S | EtS  | H    |
| 72  | CH | H   | Cl  | H   | (iv)  | S | CF3  | H    |
| 73  | CH | Cl  | H   | H   | (iv)  | S | CF3  | H    |
| 74  | CH | H   | F   | H   | (iv)  | S | tBu  | H    |
| 75  | CH | CH3 | CH3 | H   | (iv)  | S | tBu  | H    |

A: ethoxycarbonylmethyl, tBu: t-butyl, Ac: acetyl, Et: ethyl, cPr: cyclopropyl, and EtS: ethylthio.

Pharmacological Test Example 1
Measurement of Inhibitory Activity Against KDR Phosphorylation by ELISA NIH 3T3 cells expressing human KDR (Sawano A et al., Cell Growth & Differentiation, 7, 213–221 (1996), "Flt-1 but not KDR/Flk-1 tyrosine kinase is a receptor for placenta growth factor, which is related to vascular endothelial growth factor") prepared by transfection of human KDR gene were cultured in a DMEM containing 10% fetal calf serum (purchased from GIBCO BRL) within a 5% carbon dioxide incubator until 50 to 70% confluent. The harvested cells were inoculated into wells of a collagen-type one-coat 96-well flat-bottom plate, each containing the same medium, in an amount of $1.5 \times 10^4$ per well, followed by cultivation at 37° C. overnight. The medium was then replaced by a DMEM medium containing 0.1% fetal calf serum. A solution of a test compound in dimethyl sulfoxide was added to each well, and the cultivation was continued at 37° C. for additional one hr. A human recombinant vascular endothelial growth factor (hereinafter abbreviated to "VEGF") was added to a final concentration of 100 ng/ml, and the stimulation of cells was carried out at 37° C. for 2 min. The medium was removed, the cells were washed with phosphate buffered saline (pH 7.4), and 50 μl of a solubilization buffer (20 mM HEPES (pH 7.4), 150 mM NaCl, 0.2% Triton X-100, 10% glycerol, 5 mM sodium orthovanadylate, 5 mM disodium ethylenediaminetetraacetate, and 2 mM $Na_4P_2O_7$) was then added thereto. The mixture was shaken at 4° C. for 2 hr to prepare a cell extract.

Separately, phosphate buffered saline (50 μl, pH 7.4) containing 5 μg/ml of an anti-phospho-tyrosine antibody (PY20; purchased from Transduction Laboratories) was added to a microplate for ELISA (Maxisorp; purchased from NUNC), followed by standing at 4° C. overnight to form a solid phase on the wells. After washing of the plate, 300 μl of a blocking solution was added, followed by standing at room temperature for 2 hr to perform blocking. After washing, the whole quantity of the cell extract was transferred to the wells, and the plate was then allowed to stand at 4° C. overnight. After washing, an anti-KDR antibody (purchased from Santa Cruz) was allowed to react at room temperature for one hr, and, after washing, a peroxidase-labeled anti-rabbit Ig antibody (purchased from Amersham) was allowed to react at room temperature for one hr. After washing, a chromophoric substrate for peroxidase (purchased from Sumitomo Bakelite Co., Ltd.) was added thereto to initiate a reaction. After a suitable level of color development, a reaction termination solution was added to stop the reaction, and the absorbance at 450 nm was measured with a microplate reader. The KDR phosphorylation activity for each well was determined by presuming the absorbance with the addition of VEGF and without the addition of the medicament to be 100% KDR phosphorylation activity and the absorbance without the addition of the medicament and VEGF to be 0% KDR phosphorylation activity. The concentration of the test compound was varied on several levels, the inhibition (%) of KDR phosphorylation was determined for each case, and the concentration of the test compound necessary for inhibiting 50% of KDR phosphorylation ($IC_{50}$) was calculated.

The inhibitory activity against KDR phosphorylation for representative examples of a group of compounds according to the present invention is shown in Table 2.

TABLE 2

|        | $IC_{50}$, μM |
|--------|---------------|
| Ex. 1  | 0.0023        |
| Ex. 2  | 0.002         |
| Ex. 3  | <0.001        |
| Ex. 4  | <0.001        |
| Ex. 5  | <0.001        |
| Ex. 6  | <0.001        |
| Ex. 9  | 0.0002        |
| Ex. 10 | 0.0036        |
| Ex. 11 | 0.0093        |
| Ex. 12 | <0.001        |
| Ex. 13 | 0.0022        |
| Ex. 14 | 0.0044        |
| Ex. 15 | 0.0134        |
| Ex. 16 | 0.0549        |
| Ex. 17 | 0.0049        |
| Ex. 18 | 0.0697        |
| Ex. 19 | 0.0175        |
| Ex. 20 | 0.0042        |
| Ex. 21 | 0.0004        |

TABLE 2-continued

| | $IC_{50}, \mu M$ |
|---|---|
| Ex. 22 | <0.001 |
| Ex. 23 | <0.001 |
| Ex. 24 | 0.001 |
| Ex. 25 | 0.0019 |
| Ex. 26 | 0.005 |
| Ex. 27 | 0.0003 |
| Ex. 28 | 0.0003 |
| Ex. 29 | 0.0494 |
| Ex. 30 | 0.0286 |
| Ex. 31 | 0.0339 |
| Ex. 32 | 0.0037 |
| Ex. 33 | 0.0211 |
| Ex. 34 | 0.0028 |
| Ex. 35 | 0.0019 |
| Ex. 36 | 0.0012 |
| Ex. 37 | 0.0019 |
| Ex. 38 | <0.001 |
| Ex. 39 | <0.001 |
| Ex. 40 | <0.001 |
| Ex. 42 | 0.0047 |
| Ex. 43 | <0.001 |
| Ex. 44 | 0.0011 |
| Ex. 45 | <0.001 |
| Ex. 46 | 0.0074 |
| Ex. 47 | 0.0028 |
| Ex. 48 | 0.0044 |
| Ex. 49 | 0.0031 |
| Ex. 50 | 0.0063 |
| Ex. 51 | 0.0037 |
| Ex. 52 | 0.013 |
| Ex. 53 | 0.0012 |
| Ex. 58 | 0.036 |
| Ex. 59 | 0.0013 |
| Ex. 60 | <0.001 |
| Ex. 62 | 0.0015 |
| Ex. 63 | <0.001 |
| Ex. 64 | 0.0015 |
| Ex. 65 | <0.001 |
| Ex. 66 | 0.0037 |
| Ex. 67 | 0.0024 |
| Ex. 68 | 0.018 |
| Ex. 69 | 0.0041 |
| Ex. 70 | 0.0022 |
| Ex. 71 | 0.0031 |
| Ex. 72 | 0.0029 |
| Ex. 73 | 0.021 |
| Ex. 74 | 0.003 |
| Ex. 75 | 0.0045 |

Pharmacological Test Example 2
Measurement of Antitumor Activity Against Human Pulmonary Carcinoma Cells (LC-6)

Human pulmonary carcinoma cells (LC-6) (obtained from Central Laboratories for Experimental Animals) were transplanted into nude mice. When the tumor volume became about 100 mm³, the mice were grouped so that each group consisted of four mice and the average tumor volume was even among the groups. A test compound was orally administered at a dose of 20 mg/kg to the test groups every day once a day for 9 days, while only a vehicle was administered to a control group in the manner as in the test groups. The tumor growth inhibition rate (TGIR) was calculated as follows: The tumor growth inhibition rate (TGIR)=(1−TX/CX)×100 wherein CX represents the volume of tumor at day X for the control group when the tumor volume at the first day of the administration was presumed to be 1; and TX represents the tumor volume for test compound administration groups.

The tumor growth inhibition rate for representative examples of the compounds according to the present invention is shown in Table 3.

TABLE 3

| | TGIR, % |
|---|---|
| Ex. 3 | 39.5 |
| Ex. 4 | 55.4 |
| Ex. 5 | 29.5 |
| Ex. 6 | 29.3 |
| Ex. 9 | 63.5 |
| Ex. 21 | 66.6 |
| Ex. 22 | 43.8 |
| Ex. 23 | 51.7 |
| Ex. 24 | 39.8 |
| Ex. 25 | 18.8 |
| Ex. 28 | 66.3 |
| Ex. 29 | 66.1 |
| Ex. 38 | 92.0 |
| Ex. 39 | 64.0 |
| Ex. 40 | 34.2 |
| Ex. 50 | 11.9 |
| Ex. 51 | 45.6 |
| Ex. 52 | 20.7 |
| Ex. 53 | 14.4 |
| Ex. 58 | 13.4 |
| Ex. 69 | 23.3 |

Pharmacological Test Example 3
Measurement of Antitumor Activity Against Human Pulmonary Carcinoma Cells (LC-6) Using Nude Rats Human pulmonary carcinoma cells (LC-6) (obtained from Central Laboratories for Experimental Animals) were transplanted into nude rats. When the tumor volume became about 700 mm³, the rats were grouped so that each group consisted of four rats and the average tumor volume was even among the groups. A test compound was orally administered at doses of 0.2, 0.5, 1.0, and 5.0 mg/kg to the test groups every day once a day for 14 days, while only a vehicle was administered to a control group in the manner as in the test groups. The tumor growth inhibition rate (TGIR) was calculated as follows: The tumor growth inhibition rate (TGIR)=(1−TX/CX)×100 wherein CX represents the volume of tumor at day X for the control group when the tumor volume at the first day of the administration was presumed to be 1; and TX represents the tumor volume for test compound administration groups.

The tumor growth inhibition rate for representative examples of the compounds according to the present invention is shown in Table 4.

TABLE 4

| Compound | Dose, mg/kg | TGIR, % |
|---|---|---|
| 4 | 0.2 | 62 |
| 4 | 0.5 | 80 |
| 4 | 1 | 88 |
| 27 | 5 | 82 |
| 28 | 5 | 59 |
| 38 | 5 | 78 |

Pharmacological Test Example 4
Measurement of Antitumor Activity of Compound 4 Against Human Pulmonary Carcinoma Cells (A549) or Human Colon Carcinoma Cells (LS174T) Using Nude Mice Human colon carcinoma cells (LS174T) (obtained from American Type Culture Collection) or human pulmonary carcinoma cells (A549) (obtained from RIKEN Cell Bank) were transplanted into nude mice. When the tumor volume became about 150 mm³, the mice were grouped so that each group consisted of four mice and the average tumor volume was even among the groups. A test compound was orally administered at doses of 5 and 20 mg/kg to the test groups every day once a day for 9 days, while only a vehicle was administered to a control group in the manner as in the test groups. The tumor growth inhibition rate (TGIR) was calculated as follows: The tumor growth inhibition rate (TGIR)=(1−TX/CX)×100 wherein CX represents the volume of tumor at day X for the control group when the tumor volume at the first day of the administration was presumed to be 1; and TX represents the tumor volume for test compound administration groups.

The tumor growth inhibition rate for representative examples of the compounds according to the present invention is shown in Table 5.

TABLE 5

| Carcinoma cells | Dose, mg/kg | TGIR, % |
|---|---|---|
| LS174T | 5 | 65 |
| A549 | 20 | 65 |

What is claimed is:

1. A compound represented by formula (I) or a pharmaceutically acceptable salt or solvate thereof:

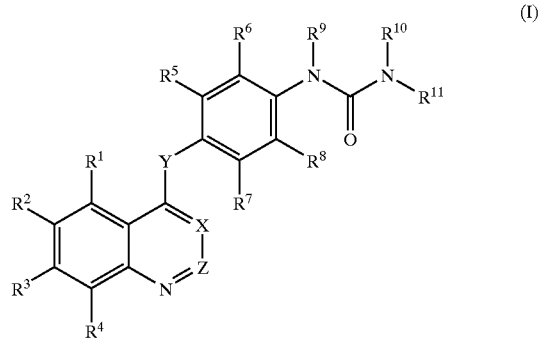

(I)

wherein

X and Z represent CH;

Y represents O or S;

$R^1$, $R^2$, and $R^3$, which may be the same or different, represent a hydrogen atom, $C_{1-6}$ alkyl, $C_{1-6}$ alkoxy, $C_{2-6}$ alkenyl, $C_{2-6}$ alkynyl, nitro, or amino and the $C_{1-6}$ alkyl, $C_{1-6}$ alkoxy, $C_{2-6}$ alkenyl, and $C_{2-6}$ alkynyl groups are optionally substituted by a halogen atom; hydroxyl; $C_{1-4}$ alkyl; $C_{1-4}$ alkoxycarbonyl; amino on which one or two hydrogen atoms are optionally substituted by $C_{1-4}$ alkyl optionally substituted by hydroxyl or $C_{1-4}$ alkoxy; group $R^{12}R^{13}N-C(=O)-O-$ wherein $R^{12}$ and $R^{13}$, which may be the same or different, represent a hydrogen atom or $C_{1-4}$ alkyl optionally substituted by hydroxyl or $C_{1-4}$ alkoxy; or group $R^{14}-(S)_m-$ wherein $R^{14}$ represents a saturated or unsaturated three- to seven-membered carbocyclic or heterocyclic group optionally substituted by $C_{1-4}$ alkyl and m is 0 or 1;

$R^4$ represents a hydrogen atom;

$R^5$, $R^6$, $R^7$, and $R^8$, which may be the same or different, represent a hydrogen atom, a halogen atom, $C_{1-4}$ alkyl, $C_{1-4}$ alkoxy, $C_{1-4}$ alkylthio, trifluoromethyl, nitro, or amino;

$R^9$ and $R^{10}$, which may be the same or different, represent a hydrogen atom, $C_{1-6}$ alkyl, or $C_{1-4}$ alkylcarbonyl and the alkyl portion of the $C_{1-6}$ alkyl or $C_{1-4}$ alkylcarbonyl group is optionally substituted by a halogen atom; $C_{1-4}$ alkoxy; amino optionally substituted by $C_{1-4}$ alkyl optionally substituted by $C_{1-4}$ alkoxy; or a saturated or unsaturated three- to seven-membered carbocyclic or heterocyclic group; and $R^{11}$ represents azolyl on which one or more hydrogen atoms are optionally substituted by a halogen atom; $C_{1-4}$ alkyl; $C_{1-4}$ alkoxy; $C_{1-4}$ alkylthio; trifluoromethyl; nitro; amino on which one or two hydrogen atoms are optionally substituted by $C_{1-4}$ alkyl group(s) which may be the same or different; $C_{1-4}$ alkoxycarbonyl $C_{1-4}$ alkyl, $C_{1-4}$ alkylcarbonyl, or $C_{3-5}$ cyclic alkyl.

2. The compound according to claim 1, wherein $R^1$, $R^9$, and $R^{10}$ represent a hydrogen atom.

3. The compound according to claim 1, which is represented by formula (Ia):

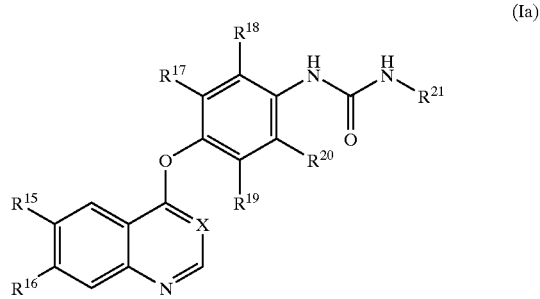

(Ia)

wherein

X represents CH, $R^{15}$ and $R^{16}$, which may be the same or different, represent $C^{1-6}$ alkoxy, $R^{17}$, $R^{18}$, $R^{19}$, and $R^{20}$, which may be the same or different, represent a hydrogen atom, a halogen atom, $C_{1-4}$ alkyl, $C_{1-4}$ alkoxy, $C_{1-4}$ alkylthio, trifluoromethyl, nitro, or amino, $R^{21}$ represents azolyl on which one or more hydrogen atoms are optionally substituted by a halogen atom; $C_{1-4}$ alkyl; $C_{1-4}$ alkoxy; $C_{1-4}$ alkylthio; trifluoromethyl; nitro; amino on which one or two hydrogen atoms are optionally substituted by $C_{1-4}$ alkyl group(s) which may be the same or different; $C_{1-4}$ alkoxycarbonyl $C_{1-4}$ alkyl; $C_{1-4}$ alkylcarbonyl; or $C_{3-5}$ cyclic alkyl.

4. The compound according to claim 3, wherein $R^{15}$ and $R^{16}$ represent methoxy.

5. The compound according to claim 3, wherein at least one of $R^{17}$, $R^{18}$, $R^{19}$, and $R^{20}$ represents a halogen atom.

6. The compound according to claim 3, wherein at least one of $R^{17}$, $R^{18}$, $R^{19}$, and $R^{20}$ represents a chlorine or fluorine atom.

7. The compound according to claim 3, wherein at least one of $R^{17}$, $R^{18}$, $R^{19}$, and $R^{20}$ represents $C_{1-4}$ alkyl.

8. The compound according to claim 3, wherein at least one of $R^{17}$, $R^{18}$, $R^{19}$, and $R^{20}$ represents $C_{1-4}$ alkoxy.

9. The compound according to claim 3, wherein at least one of $R^{17}$, $R^{18}$, $R^{19}$, and $R^{20}$ represents $C_{1-4}$ alkylthio, trifluoromethyl, nitro, or amino.

10. The compound according to claim 3, wherein $R^{21}$ represents group (i):

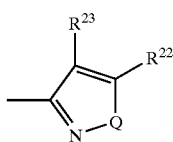

wherein Q represents O, S, or NH, and $R^{22}$ and $R^{23}$, which may be the same or different, represent a hydrogen atom; a halogen atom; $C_{1-4}$ alkyl; $C_{1-4}$ alkoxy; $C_{1-4}$ alkylthio; trifluoromethyl; nitro; amino on which one or two hydrogen atoms are optionally substituted by $C_{1-4}$ alkyl group(s) which may be the same or different; $C_{1-4}$ alkoxycarbonyl $C_{1-4}$ alkyl; $C_{1-4}$ alkylcarbonyl; or $C_{3-5}$ cyclic alkyl.

11. The compound according to claim 3, wherein $R^{21}$ represent group (ii):

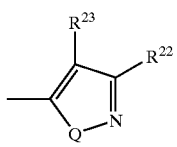

wherein Q represents O, S, or NH, and $R^{22}$ and $R^{23}$, which may be the same or different, represent a hydrogen atom; a halogen atom; $C_{1-4}$ alkyl; $C_{1-4}$ alkoxy; $C_{1-6}$ alkylthio; trifluoromethyl; nitro; amino on which one or two hydrogen atoms are optionally substituted by $C_{1-4}$ alkyl group(s) which may be the same or different; $C_{1-4}$ alkoxycarbonyl $C_{1-4}$ alkyl; $C_{1-4}$ alkylcarbonyl; or $C_{3-5}$ cyclic alkyl.

12. The compound according to claim 3, wherein $R^{21}$ represent group (iii):

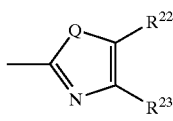

wherein Q represents O, S, or NH, and $R^{22}$ and $R^{23}$, which may be the same or different, represent a hydrogen atom; a halogen atom; $C_{1-4}$ alkyl; $C_{1-4}$ alkoxy; $C_{1-4}$ alkylthio; trifluoromethyl; nitro; amino on which one or two hydrogen atoms are optionally substituted by $C_{1-4}$ alkyl group(s) which may be the same or different; $C_{1-4}$ alkoxycarbonyl $C_{1-4}$ alkyl; $C_{1-4}$ alkylcarbonyl; or $C_{3-5}$ cyclic alkyl.

13. The compound according to claim 3, wherein $R^{21}$ represents group (iv):

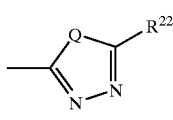

wherein Q represents O, S, or NH, and $R^{22}$ represents a hydrogen atom; a halogen atom; $C_{1-4}$ alkyl; $C_{1-4}$ alkoxy; $C_{1-4}$ alkylthio; trifluoromethyl; nitro; amino on which one or two hydrogen atoms are optionally substituted by $C_{1-4}$ alkyl group(s) which may be the same or different; $C_{1-4}$ alkoxycarbonyl $C_{1-4}$ alkyl; $C_{1-4}$ alkylcarbonyl; or $C_{3-5}$ cyclic alkyl.

14. The compound according to claim 3, wherein $R^{21}$ represents optionally substituted thiazolyl.

15. The compound according to claim 3, wherein $R^{21}$ represents optionally substituted oxazolyl.

16. The compound according to claim 3, wherein $R^{21}$ represents optionally substituted isothiazolyl.

17. The compound according to claim 3, wherein $R^{21}$ represents optionally substituted isoxazolyl.

18. The compound according to claim 3, wherein $R^{21}$ represents optionally substituted pyrazolyl.

19. The compound according to claim 3, wherein $R^{21}$ represents optionally substituted 1,2,4-thiadiazolyl.

20. The compound according to claim 3, wherein $R^{21}$ represents optionally substituted 1,2,4-oxadiazolyl.

21. The compound according to claim 3, wherein $R^{21}$ represents optionally substituted 1,3,4-thiadiazolyl.

22. The compound according to claim 3, wherein $R^{21}$ represents optionally substituted 1,3,4-oxadiazolyl.

23. The compound according to claim 3, which is represented by formula (Ib):

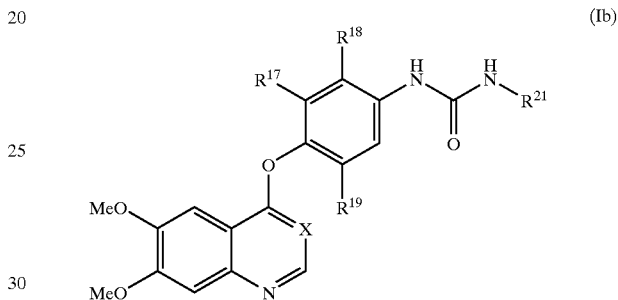

wherein

MeO represents methoxy;

X represents CH;

$R^{17}$, $R^{18}$, $R^{19}$, which may be the same or different, represent a hydrogen atom, a halogen atom, $C_{1-4}$ alkyl, $C_{1-4}$ alkoxy, $C_{1-4}$ alkylthio, trifluoromethyl, nitro, or amino; and $R^{21}$ represents group (i), (ii),(iii), or (iv):

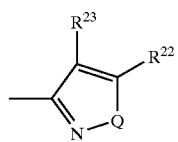

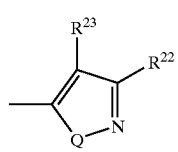

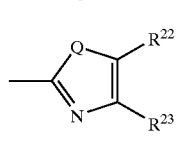

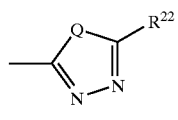

wherein Q represents O, S, or NH, and $R^{22}$ and $R^{23}$, which may be the same or different, represent a hydrogen atom; a halogen atom; $C_{1-4}$ alkyl; $C_{1-4}$ alkoxy; $C_{1-4}$ alkylthio; trifluoromethyl; nitro; amino on which one or two hydrogen atoms are optionally substituted by $C_{1-4}$ alkyl group(s) which may be the same or different; $C_{1-4}$ alkoxycarbonyl $C_{1-4}$ alkyl; $C_{1-4}$ alkylcarbonyl; or $C_{3-5}$ cyclic alkyl.

24. The compound according to claim 23, wherein $R^{21}$ represents group (iii) wherein Q represents S.

25. The compound according to claim 24, wherein both $R^{22}$ and $R^{23}$ represent a hydrogen atom, or one of $R^{22}$ and $R^{23}$ represents a hydrogen atom and the other represents $C_{1-4}$ alkyl.

26. The compound according to claim 1, which is N-{2-chloro-4-[(6,7-dimethoxy-4-quinolyl)oxy]-phenyl}-N'-(5-methyl-3-isoxazolyl)urea, or a pharmaceutically acceptable salt or solvate thereof.

27. A pharmaceutical composition comprising the compound according to claim 1 or a pharmaceutically acceptable salt or solvate thereof as an active ingredient.

28. A method for treating a disease selected from the group consisting of diabetic retinopathy, chronic rheumatism, psoriasis, and atherosclerosis, comprising administering a therapeutically effective amount of the compound according to claim 1 or a pharmaceutically acceptable salt or solvate thereof to a mammal.

29. A method for inhibiting the angiogenesis of blood vessels, comprising bringing the compound according to claim 1 or a pharmaceutically acceptable salt or solvate thereof into contact with vascular endothelial cells.

30. A method for treating Kaposi's Sarcoma comprising administering a therapeutically effective amount of the compound according to claim 1 or a pharmaceutically acceptable salt or solvate thereof to a mammal.

31. A method for treating a malignant tumor comprising administering a therapeutically effective amount of the compound according to claim 1 or a pharmaceutically acceptable salt or solvate thereof to a mammal, wherein said malignant tumor is a lung tumor.

32. A method for treating a malignant tumor comprising administering a therapeutically effective amount of the compound according to claim 1 or a pharmaceutically acceptable salt or solvate thereof to a mammal, wherein said malignant tumor is a colon tumor.

33. The compound according to claim 1, wherein $R^{11}$ represents

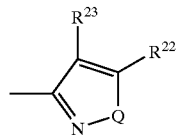

(i)

wherein Q represents O, S, or NH, and $R^{22}$ and $R^{23}$, which may be the same or different, represent a hydrogen atom; a halogen atom; $C_{1-4}$ alkyl; $C_{1-4}$ alkoxy; $C_{1-4}$ alkylthio; trifluoromethyl; nitro; amino on which one or two hydrogen atoms are optionally substituted by $C_{1-4}$ alkyl group(s) which may be the same or different; $C_{1-4}$ alkoxycarbonyl $C_{1-4}$ alkyl; $C_{1-4}$ alkylcarbonyl; or $C_{3-5}$ cyclic alkyl.

34. The compound according to claim 33, wherein Q represents O, $R^{22}$ represents $C_{1-4}$ alkyl, and $R^{23}$ represents hydrogen.

35. The compound according to claim 34, wherein $R^{22}$ represents methyl.

36. The compound according to claim 1, wherein $R^{11}$ represents optionally substituted isoxazolyl.

37. The compound according to claim 10, wherein Q represents O, $R^{22}$ represents $C_{1-4}$ alkyl, and $R^{23}$ represents hydrogen.

38. The compound according to claim 37, wherein $R^{22}$ represents methyl.

39. The compound according to claim 10, wherein $R^{21}$ represents optionally substituted isoxazolyl.

40. The compound according to claim 23, wherein $R^{18}$ represents halogen and $R^{17}$ and $R^{19}$ represent hydrogen.

41. The compound according to claim 23, wherein $R^{18}$ represents chlorine and $R^{17}$ and $R^{19}$ represent hydrogen.

42. The compound according to claim 23, wherein $R^{21}$ represents group (i).

43. The compound according to claim 42, wherein Q represents O.

44. The compound according to claim 43, wherein both $R^{22}$ and $R^{23}$ represent hydrogen, or one of $R^{22}$ and $R^{23}$ represents hydrogen and the other represents $C_{1-4}$ alkyl.

45. The compound according to claim 44, wherein $R^{22}$ represents $C_{1-4}$ alkyl and $R^{23}$ represents hydrogen.

46. The compound according to claim 45, wherein $R^{22}$ represents methyl.

47. The compound according to claim 23, wherein $R^{21}$ represents group (i), $R^{18}$ represents halogen, $R^{17}$ and $R^{19}$ represent hydrogen, and Q represents O.

48. The compound according to claim 23, wherein $R^{21}$ represents group (i), $R^{18}$ represents chlorine, $R^{17}$ and $R^{19}$ represent hydrogen, and Q represents O.

49. The compound according to claim 23, wherein $R^{21}$ represents group (i), $R^{22}$ represents $C_{1-4}$ alkyl, $R^{23}$ represents hydrogen, and Q represents O.

50. The compound according to claim 23, wherein $R^{21}$ represents group (i), $R^{22}$ represents methyl, $R^{23}$ represents hydrogen, and Q represents O.

51. The compound according to claim 23, wherein $R^{21}$ represents group (i), $R^{18}$ represents halogen, $R^{17}$ and $R^{19}$ represent hydrogen, Q represents O, $R^{22}$ represents $C_{1-4}$ alkyl, and $R^{23}$ represents hydrogen.

52. The compound according to claim 23, wherein $R^{21}$ represents group (i), $R^{18}$ represents chlorine, $R^{17}$ and $R^{19}$ represent hydrogen, Q represents O, $R^{22}$ represents $C_{1-4}$ alkyl, and $R^{23}$ represents hydrogen.

53. The compound according to claim 23, wherein $R^{21}$ represents group (i), $R^{18}$ represents halogen, $R^{17}$ and $R^{19}$ represent hydrogen, Q represents O, $R^{22}$ represents methyl, and $R^{23}$ represents hydrogen.

54. The compound according to claim 1, which is N-{3-chloro-4-[(6,7-dimethoxy-4-quinolyl)-oxy]phenyl}-N'-(3-isoxazolyl)urea or a pharmaceutically acceptable salt or solvate thereof.

55. The compound according to claim 1, which is N-{4-[(6,7-dimethoxy-4-quinolyl)oxy]-3-fluorophenyl}-N'-(3-isoxazolyl)urea or a pharmaceutically acceptable salt or solvate thereof.

56. The compound according to claim 1, which is N-{4-[(6,7-dimethoxy-4-quinolyl)oxy]-3-fluorophenyl}-N'-(5-methyl-3-isoxazolyl)urea or a pharmaceutically acceptable salt or solvate thereof.

57. The compound according to claim 1, which is N-{4-[(6,7-dimethoxy-4-quinolyl)oxy]-2-fluorophenyl}-N'-(5-methyl-3-isoxazolyl)urea or a pharmaceutically acceptable salt or solvate thereof.

* * * * *